United States Patent
Grauzer et al.

(10) Patent No.: US 8,777,710 B2
(45) Date of Patent: *Jul. 15, 2014

(54) APPARATUS, SYSTEM, METHOD, AND COMPUTER-READABLE MEDIUM FOR CASINO CARD HANDLING WITH MULTIPLE HAND RECALL FEATURE

(75) Inventors: Attila Grauzer, Las Vegas, NV (US); Feraidoon Bourbour, Eden Prairie, MN (US); Mark L. Yoseloff, Henderson, NV (US)

(73) Assignee: SHFL Entertainment, Inc., Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/311,166

(22) Filed: Dec. 5, 2011

(65) Prior Publication Data
US 2012/0074646 A1    Mar. 29, 2012

Related U.S. Application Data

(63) Continuation of application No. 11/810,864, filed on Jun. 6, 2007, now Pat. No. 8,070,574.

(51) Int. Cl.
*A63F 9/24*    (2006.01)
(52) U.S. Cl.
USPC ............................ 463/12; 463/13; 273/149 R
(58) Field of Classification Search
USPC ................................... 273/149 R; 463/12, 13
See application file for complete search history.

(56) References Cited

U.S. PATENT DOCUMENTS

| 793,489 | A | 6/1905 | Williams |
| 1,014,219 | A | 1/1912 | Hall |
| 1,885,276 | A | 11/1932 | McKay |
| 2,001,220 | A | 5/1935 | Smith |
| 2,001,918 | A | 5/1935 | Nevius |
| 2,016,030 | A | 10/1935 | Woodruff et al. |
| 2,043,343 | A | 6/1936 | Warner |
| 2,065,824 | A | 12/1936 | Plass |
| 2,254,484 | A | 9/1941 | Hutchins |

(Continued)

FOREIGN PATENT DOCUMENTS

| WO | 8700764 | 2/1987 |
| WO | 9840136 | 9/1998 |
| WO | 0051076 | 8/2000 |

OTHER PUBLICATIONS

Scarne's Encyclopedia of Games by John Scarne, 1973, "Super Contract Bridge", p. 153.

(Continued)

*Primary Examiner* — Pierre E Elisca
(74) *Attorney, Agent, or Firm* — TraskBritt

(57) ABSTRACT

Apparatuses, systems, methods, and computer-readable media are disclosed for detecting, storing, and retrieving information about the composition of present and past hands of cards in a casino table game. The method includes causing a card-handling device to substantially automatically generate a plurality of hands wherein each hand includes one or more cards. Card information is identified that includes a rank and a suit of each card as each card moves through the card-handling device. A play history is maintained of a card composition of more than one round wherein the card composition of each round includes the cards in each hand of each round. The card information of at least one hand from at least one round may be displayed.

32 Claims, 10 Drawing Sheets

(56) References Cited

U.S. PATENT DOCUMENTS

| | | |
|---|---|---|
| 2,328,153 A | 8/1943 | Laing |
| 2,328,879 A | 9/1943 | Isaacson |
| 2,364,413 A | 12/1944 | Wittel |
| 2,778,644 A | 1/1957 | Stephenson |
| 2,937,739 A | 5/1960 | Levy |
| 2,950,005 A | 8/1960 | MacDonald |
| 3,147,978 A | 9/1964 | Sjostrand |
| 3,235,741 A | 2/1966 | Plaisance |
| 3,312,473 A | 4/1967 | Friedman et al. |
| 3,530,968 A | 9/1970 | Palmer |
| 3,595,388 A | 7/1971 | Castaldi |
| 3,690,670 A | 9/1972 | Cassady et al. |
| 3,716,238 A | 2/1973 | Porter |
| 3,897,954 A | 8/1975 | Erickson et al. |
| 3,944,230 A | 3/1976 | Fineman |
| 4,159,581 A | 7/1979 | Lichtenberg |
| 4,232,861 A | 11/1980 | Maul |
| 4,310,160 A | 1/1982 | Willette |
| 4,361,393 A | 11/1982 | Noto |
| 4,368,972 A | 1/1983 | Naramore |
| 4,385,827 A | 5/1983 | Naramore |
| 4,388,994 A | 6/1983 | Suda et al. |
| 4,397,469 A | 8/1983 | Carter |
| 4,494,197 A | 1/1985 | Troy et al. |
| 4,497,488 A | 2/1985 | Plevyak et al. |
| 4,512,580 A | 4/1985 | Matviak |
| 4,513,969 A | 4/1985 | Samsel |
| 4,515,367 A | 5/1985 | Howard |
| 4,534,562 A | 8/1985 | Cuff et al. |
| 4,566,782 A | 1/1986 | Britt et al. |
| 4,586,712 A | 5/1986 | Lorber et al. |
| 4,659,082 A | 4/1987 | Greenberg |
| 4,662,637 A | 5/1987 | Pfeiffer |
| 4,667,959 A | 5/1987 | Pfeiffer et al. |
| 4,741,524 A | 5/1988 | Bromage |
| 4,750,743 A | 6/1988 | Nicoletti |
| 4,755,941 A | 7/1988 | Bacchi |
| 4,759,448 A | 7/1988 | Kawabata |
| 4,770,421 A | 9/1988 | Hoffman |
| 4,807,884 A | 2/1989 | Breeding |
| 4,822,050 A | 4/1989 | Normand et al. |
| 4,832,342 A | 5/1989 | Plevyak et al. |
| 4,876,000 A | 10/1989 | Mikhail |
| 4,900,009 A | 2/1990 | Kitahara et al. |
| 4,926,327 A | 5/1990 | Sidley |
| 4,951,950 A | 8/1990 | Normand et al. |
| 4,969,648 A | 11/1990 | Hollinger et al. |
| 4,995,615 A | 2/1991 | Cheng |
| 5,000,453 A | 3/1991 | Stevens et al. |
| 5,067,713 A | 11/1991 | Soules et al. |
| 5,081,487 A | 1/1992 | Hoyer et al. |
| 5,121,192 A | 6/1992 | Kazui |
| 5,121,921 A | 6/1992 | Friedman et al. |
| 5,179,517 A | 1/1993 | Sarbin et al. |
| 5,199,710 A | 4/1993 | Lamle |
| 5,209,476 A | 5/1993 | Eiba |
| 5,224,712 A | 7/1993 | Laughlin et al. |
| 5,240,140 A | 8/1993 | Huen |
| 5,257,179 A | 10/1993 | DeMar |
| 5,261,667 A | 11/1993 | Breeding |
| 5,275,411 A | 1/1994 | Breeding |
| 5,276,312 A | 1/1994 | McCarthy |
| 5,283,422 A | 2/1994 | Storch et al. |
| 5,288,081 A | 2/1994 | Breeding |
| 5,299,089 A | 3/1994 | Lwee |
| 5,303,921 A | 4/1994 | Breeding |
| 5,356,145 A | 10/1994 | Verschoor |
| 5,362,053 A | 11/1994 | Miller |
| 5,374,061 A | 12/1994 | Albrecht |
| 5,382,024 A | 1/1995 | Blaha |
| 5,382,025 A | 1/1995 | Sklansky et al. |
| 5,390,910 A | 2/1995 | Mandel et al. |
| 5,431,399 A | 7/1995 | Kelley |
| 5,437,462 A | 8/1995 | Breeding |
| 5,445,377 A | 8/1995 | Steinbach |
| 5,470,079 A | 11/1995 | LeStrange et al. |
| 5,524,888 A | 6/1996 | Heidel |
| 5,584,483 A | 12/1996 | Sines et al. |
| 5,586,766 A | 12/1996 | Forte et al. |
| 5,586,936 A | 12/1996 | Bennett et al. |
| 5,605,334 A | 2/1997 | McCrea, Jr. |
| 5,613,912 A | 3/1997 | Slater |
| 5,651,548 A | 7/1997 | French et al. |
| 5,655,961 A | 8/1997 | Acres et al. |
| 5,669,816 A | 9/1997 | Garczynski et al. |
| 5,676,372 A | 10/1997 | Sines et al. |
| 5,681,039 A | 10/1997 | Miller |
| 5,683,085 A | 11/1997 | Johnson et al. |
| 5,690,324 A | 11/1997 | Otomo et al. |
| 5,692,748 A | 12/1997 | Frisco et al. |
| 5,695,189 A | 12/1997 | Breeding et al. |
| 5,707,287 A | 1/1998 | McCrea, Jr. |
| 5,718,427 A | 2/1998 | Cranford et al. |
| 5,722,893 A | 3/1998 | Hill et al. |
| 5,735,525 A | 4/1998 | McCrea, Jr. |
| 5,735,742 A | 4/1998 | French |
| 5,772,505 A | 6/1998 | Garczynski et al. |
| 5,779,546 A | 7/1998 | Meissner et al. |
| 5,781,647 A | 7/1998 | Fishbine et al. |
| 5,788,574 A | 8/1998 | Ornstein et al. |
| 5,803,808 A | 9/1998 | Strisower |
| 5,836,775 A | 11/1998 | Hiyama et al. |
| 5,911,626 A | 6/1999 | McCrea, Jr. |
| 5,919,090 A | 7/1999 | Mothwurf |
| 5,936,222 A | 8/1999 | Korsunsky et al. |
| 5,941,769 A | 8/1999 | Order |
| 5,944,310 A | 8/1999 | Johnson et al. |
| D414,527 S | 9/1999 | Tedham |
| 5,985,305 A | 11/1999 | Peery et al. |
| 5,989,122 A | 11/1999 | Roblejo |
| 6,015,311 A | 1/2000 | Benjamin et al. |
| 6,019,368 A | 2/2000 | Sines et al. |
| 6,039,650 A | 3/2000 | Hill |
| 6,068,258 A | 5/2000 | Breeding et al. |
| 6,069,564 A | 5/2000 | Hatano et al. |
| 6,071,190 A | 6/2000 | Weiss et al. |
| 6,093,103 A | 7/2000 | McCrea, Jr. |
| 6,117,012 A | 9/2000 | McCrea, Jr. |
| 6,126,166 A | 10/2000 | Lorson et al. |
| 6,127,447 A | 10/2000 | Mitry et al. |
| 6,139,014 A | 10/2000 | Breeding et al. |
| 6,149,154 A | 11/2000 | Grauzer et al. |
| 6,154,131 A | 11/2000 | Jones, II et al. |
| 6,165,069 A | 12/2000 | Sines et al. |
| 6,165,072 A | 12/2000 | Davis et al. |
| 6,213,310 B1 | 4/2001 | Wennersten et al. |
| 6,217,447 B1 | 4/2001 | Lofink et al. |
| 6,236,223 B1 | 5/2001 | Brady et al. |
| 6,250,632 B1 | 6/2001 | Albrecht |
| 6,254,096 B1 | 7/2001 | Grauzer et al. |
| 6,254,484 B1 | 7/2001 | McCrea, Jr. |
| 6,267,248 B1 | 7/2001 | Johnson et al. |
| 6,267,648 B1 | 7/2001 | Katayama et al. |
| 6,267,671 B1 | 7/2001 | Hogan |
| 6,270,404 B2 | 8/2001 | Sines et al. |
| 6,293,864 B1 | 9/2001 | Romero |
| 6,299,167 B1 | 10/2001 | Sines et al. |
| 6,299,536 B1 | 10/2001 | Hill |
| 6,313,871 B1 | 11/2001 | Schubert |
| 6,325,373 B1 | 12/2001 | Breeding et al. |
| 6,342,830 B1 | 1/2002 | Want et al. |
| 6,346,044 B1 | 2/2002 | McCrea, Jr. |
| 6,361,044 B1 | 3/2002 | Block et al. |
| 6,403,908 B2 | 6/2002 | Stardust et al. |
| 6,443,839 B2 | 9/2002 | Stockdale et al. |
| 6,446,864 B1 | 9/2002 | Kim et al. |
| 6,460,848 B1 | 10/2002 | Soltys et al. |
| 6,517,435 B2 | 2/2003 | Soltys et al. |
| 6,517,436 B2 | 2/2003 | Soltys et al. |
| 6,520,857 B2 | 2/2003 | Soltys et al. |
| 6,527,271 B2 | 3/2003 | Soltys et al. |
| 6,530,836 B2 | 3/2003 | Soltys et al. |
| 6,530,837 B2 | 3/2003 | Soltys et al. |
| 6,532,297 B1 | 3/2003 | Lindquist |

(56) References Cited

U.S. PATENT DOCUMENTS

| | | |
|---|---|---|
| 6,533,276 B2 | 3/2003 | Soltys et al. |
| 6,533,662 B2 | 3/2003 | Soltys et al. |
| 6,568,678 B2 | 5/2003 | Breeding et al. |
| 6,579,180 B2 | 6/2003 | Soltys et al. |
| 6,579,181 B2 | 6/2003 | Soltys et al. |
| 6,582,301 B2 | 6/2003 | Hill |
| 6,582,302 B2 | 6/2003 | Romero |
| 6,585,586 B1 | 7/2003 | Romero |
| 6,585,856 B2 | 7/2003 | Zwick et al. |
| 6,588,750 B1 | 7/2003 | Grauzer et al. |
| 6,588,751 B1 | 7/2003 | Grauzer et al. |
| 6,595,857 B2 | 7/2003 | Soltys et al. |
| 6,616,535 B1 | 9/2003 | Nishizaki et al. |
| 6,622,185 B1 | 9/2003 | Johnson et al. |
| 6,629,889 B2 | 10/2003 | Mothwurf |
| 6,629,894 B1 | 10/2003 | Purton |
| 6,637,622 B1 | 10/2003 | Robinson |
| 6,638,161 B2 | 10/2003 | Soltys et al. |
| 6,645,068 B1 | 11/2003 | Kelly et al. |
| 6,645,077 B2 | 11/2003 | Rowe |
| 6,651,981 B2 | 11/2003 | Grauzer et al. |
| 6,651,982 B1 | 11/2003 | Grauzer et al. |
| 6,652,379 B2 | 11/2003 | Soltys et al. |
| 6,655,684 B2 | 12/2003 | Grauzer et al. |
| 6,659,460 B2 | 12/2003 | Blaha et al. |
| 6,663,490 B2 | 12/2003 | Soltys et al. |
| 6,666,768 B1 | 12/2003 | Akers |
| 6,676,127 B2 | 1/2004 | Johnson et al. |
| 6,676,517 B2 | 1/2004 | Beavers |
| 6,680,843 B2 | 1/2004 | Farrow et al. |
| 6,685,567 B2 | 2/2004 | Cockerille et al. |
| 6,685,568 B2 | 2/2004 | Soltys et al. |
| 6,688,979 B2 | 2/2004 | Soltys et al. |
| 6,698,756 B1 | 3/2004 | Baker et al. |
| 6,712,696 B2 | 3/2004 | Soltys et al. |
| 6,719,634 B2 | 4/2004 | Mishina et al. |
| 6,726,205 B1 | 4/2004 | Purton |
| 6,732,067 B1 | 5/2004 | Powderly |
| 6,746,333 B1 | 6/2004 | Onda et al. |
| 6,758,751 B2 | 7/2004 | Soltys et al. |
| 6,758,757 B2 | 7/2004 | Luciano, Jr. et al. |
| 6,774,782 B2 | 8/2004 | Runyon et al. |
| 6,804,763 B1 | 10/2004 | Stockdale et al. |
| 6,834,251 B1 | 12/2004 | Fletcher |
| 6,848,616 B2 | 2/2005 | Tsirline et al. |
| 6,848,844 B2 | 2/2005 | McCue, Jr. et al. |
| 6,857,961 B2 | 2/2005 | Soltys et al. |
| 6,886,829 B2 | 5/2005 | Hessing et al. |
| 6,889,979 B2 | 5/2005 | Blaha et al. |
| 6,957,746 B2 | 10/2005 | Martin et al. |
| 6,959,925 B1 | 11/2005 | Baker et al. |
| 6,959,935 B2 | 11/2005 | Buhl et al. |
| 6,964,612 B2 | 11/2005 | Soltys et al. |
| 7,011,309 B2 | 3/2006 | Soltys et al. |
| 7,029,009 B2 | 4/2006 | Grauzer et al. |
| 7,036,818 B2 | 5/2006 | Grauzer et al. |
| 7,059,602 B2 | 6/2006 | Grauzer et al. |
| 7,066,464 B2 | 6/2006 | Blad et al. |
| 7,073,791 B2 | 7/2006 | Grauzer et al. |
| 7,084,769 B2 | 8/2006 | Bauer et al. |
| 7,106,201 B2 | 9/2006 | Tuttle |
| 7,113,094 B2 | 9/2006 | Garber et al. |
| 7,114,718 B2 | 10/2006 | Grauzer et al. |
| 7,124,947 B2 | 10/2006 | Storch |
| 7,139,108 B2 | 11/2006 | Andersen |
| 7,213,812 B2 | 5/2007 | Schubert et al. |
| 7,237,969 B2 | 7/2007 | Bartman |
| 7,255,344 B2 | 8/2007 | Grauzer et al. |
| 7,322,576 B2 | 1/2008 | Grauzer et al. |
| 7,338,044 B2 | 3/2008 | Grauzer |
| 7,367,561 B2 | 5/2008 | Blaha et al. |
| 7,384,044 B2 | 6/2008 | Grauzer et al. |
| 7,413,191 B2 | 8/2008 | Grauzer |
| 7,448,626 B2 | 11/2008 | Fleckenstein |
| 7,510,186 B2 | 3/2009 | Fleckenstein |
| 7,523,935 B2 | 4/2009 | Grauzer et al. |
| 7,661,676 B2 | 2/2010 | Smith et al. |
| 7,753,373 B2 | 7/2010 | Grauzer |
| 7,753,798 B2 | 7/2010 | Soltys |
| 7,766,332 B2 | 8/2010 | Grauzer et al. |
| 7,867,080 B2 | 1/2011 | Nicely et al. |
| 7,901,285 B2 | 3/2011 | Tran |
| 8,070,574 B2 | 12/2011 | Grauzer |
| 8,141,875 B2 | 3/2012 | Grauzer et al. |
| 2001/0036231 A1 | 11/2001 | Easwar et al. |
| 2002/0107067 A1 | 8/2002 | McGlone et al. |
| 2002/0142820 A1 | 10/2002 | Bartlett |
| 2002/0187830 A1 | 12/2002 | Stockdale et al. |
| 2003/0052450 A1 | 3/2003 | Grauzer et al. |
| 2003/0064798 A1 | 4/2003 | Grauzer et al. |
| 2003/0090059 A1 | 5/2003 | Grauzer et al. |
| 2003/0094756 A1 | 5/2003 | Grauzer et al. |
| 2003/0195025 A1 | 10/2003 | Hill |
| 2004/0067789 A1 | 4/2004 | Grauzer et al. |
| 2004/0100026 A1 | 5/2004 | Haggard |
| 2005/0035548 A1 | 2/2005 | Yoseloff et al. |
| 2005/0037843 A1 | 2/2005 | Wells et al. |
| 2005/0146093 A1 | 7/2005 | Grauzer et al. |
| 2005/0206077 A1 | 9/2005 | Grauzer et al. |
| 2005/0242500 A1 | 11/2005 | Downs, III |
| 2006/0033269 A1 | 2/2006 | Grauzer et al. |
| 2006/0046853 A1 | 3/2006 | Black |
| 2006/0063577 A1 | 3/2006 | Downs, III et al. |
| 2006/0181022 A1 | 8/2006 | Grauzer et al. |
| 2006/0279040 A1 | 12/2006 | Downs et al. |
| 2007/0006708 A1* | 1/2007 | Laakso ............................... 84/1 |
| 2007/0102879 A1* | 5/2007 | Stasson .................... 273/149 R |
| 2007/0278739 A1 | 12/2007 | Swanson |
| 2008/0006997 A1 | 1/2008 | Grauzer et al. |
| 2008/0022415 A1* | 1/2008 | Kuo et al. ....................... 726/31 |
| 2008/0111300 A1 | 5/2008 | Czyzewski |
| 2008/0113700 A1 | 5/2008 | Czyzewski et al. |
| 2008/0113783 A1 | 5/2008 | Czyzewski et al. |
| 2009/0191933 A1 | 7/2009 | French |
| 2010/0244382 A1 | 9/2010 | Snow |
| 2010/0276880 A1 | 11/2010 | Grauzer et al. |
| 2010/0314830 A1 | 12/2010 | Grauzer et al. |
| 2011/0109042 A1 | 5/2011 | Rynda |

OTHER PUBLICATIONS

Specification of Australian Patent Application No. 31577/95, filed Jan. 17, 1995, Applicants: Rodney G. Johnson et al., Title: Card Handling Apparatus.

Specification of Australian Patent Application No. Not Listed, filed Aug. 15, 1994, Applicants: Rodney G. Johnson et al., Title: Card Handling Apparatus.

PCT International Search Report and Written Opinion of the International Searching Authority for PCT/US2008/007069, dated Sep. 8, 2008, 8 pages.

PCT International Search Report for PCT/US07/15036, dated Sep. 23, 2008, 3 pages.

PCT Written Opinion for PCT/US07/15036, dated Sep. 23, 2008, 3 pages.

PCT International Search Report for PCT/US07/15035, dated Sep. 29, 2008, 3 pages.

PCT Written Opinion for PCT/US07/15035, dated Sep. 29, 2008, 3 pages.

PCT International Search Report for International Application No. PCT/US2007/022858, mailed Apr. 18, 2008.

Written Opinion of the International Searching Authority for International Application No. PCT/US2007/022858, mailed Apr. 18, 2008.

Press Release for Alliance Gaming Corp., Jul. 26, 2004—Alliance Gaming Announces Control With Galaxy Macau for New MindPlay Baccarat Table Technology, http://biz.yahoo.com/prnews.

Tracking the Tables, by Jack Bularsky, Casino Journal, May 2004, vol. 17, No. 5, pp. 44-47.

CD Labeled "Shuffler Art". Attached to this 1449 is a spreadsheet having the names of the individual files within the CD. There is a self-executing function on the CD so that, upon entering the Spread-

(56) References Cited

OTHER PUBLICATIONS sheet Table of Contents (Index), individual items may be opened directly from the spreadsheet according to the title of the document (2003).

DVD Labeled "Luciano Decl. Ex. K". This DVD includes the video taped live Declaration of Mr. Luciano (see list of patents on the 1449 or of record in the file history) taken during preparation of litigation (Oct. 23, 2003).

DVD labeled Morrill Decl. Ex. A:. This DVD includes the video taped live Declaration of Mr. Robert Morrill, a lead trial counsel for the defense, taken during preparation for litigation. He is describing the operation of the Roblejo Prototype device. See Roblejo patent in 1449 or of record (Jan. 15, 2004).

DVD Labeled "Solberg Decl. Ex. C". This DVD includes the video taped live Declaration of Mr. Solberg, a witness for the defense, taken during preparation for litigation (Dec. 22, 2003).

DVD labeled "Exhibit 1". This is a DVD taken by Shuffle Master personnel of the live operation of a CARD One2Six™ Shuffler (Oct. 7, 2003).

http://www.google.com/search?tbm=pts&q=Card+handling+devicve+with+input+and+outpu . . . Jun. 8, 2012.

http://www.google.com/search?tbm=pts&q=shuffling+zone+on+Oopposite+side+of+input+ . . . Jul. 18, 2012.

Google search for card handling device with storage area, card removing system pivoting arm and processor . . . ; http://www.google.com/?tbm=pts&hl=en; Jul. 28, 2012.

PCT International Search Report and Written Opinion of the International Searching Authority for PCT/US11/59797, dated Mar. 27, 2012, 14 pages.

Service Manual/User Manual for Single Deck Shufflers: BG1, BG2 and BG3 by Shuffle Master © 1997.

* cited by examiner

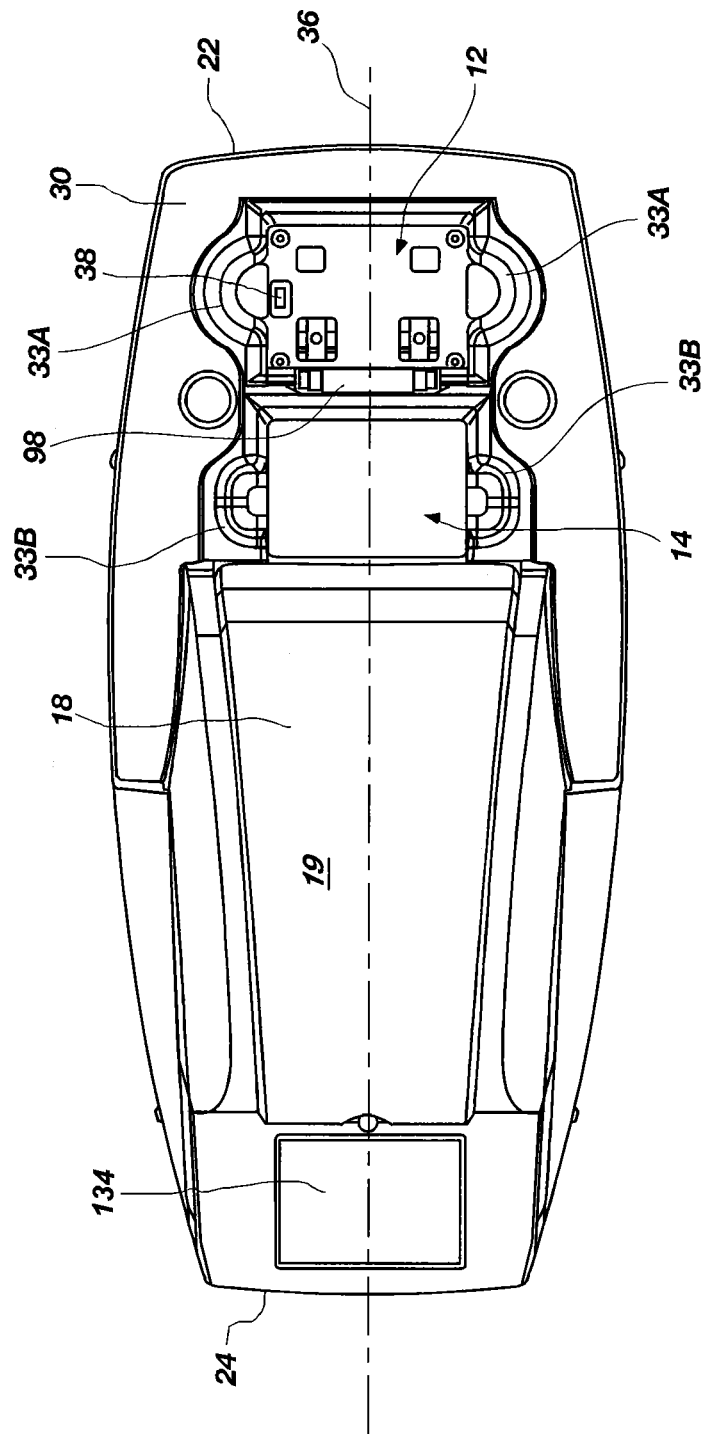

US 8,777,710 B2

APPARATUS, SYSTEM, METHOD, AND COMPUTER-READABLE MEDIUM FOR CASINO CARD HANDLING WITH MULTIPLE HAND RECALL FEATURE

CROSS-REFERENCE TO RELATED APPLICATIONS

The present application is a continuation application of U.S. patent application Ser. No. 11/810,864, filed Jun. 6, 2007, now U.S. Pat. No. 8,070,574, issued Dec. 6, 2011. The present application is also related to U.S. patent application Ser. No. 11/598,259, titled "CARD HANDLING DEVICES AND METHODS OF USING THE SAME," now U.S. Pat. No. 7,766,332, issued Aug. 3, 2010, and U.S. patent application Ser. No. 11/481,407, titled "CARD SHUFFLER WITH ADJACENT CARD INFEED AND CARD OUTPUT COMPARTMENTS," now U.S. Pat. No. 8,342,525, issued Jan. 1, 2013, the disclosure of each of which is hereby incorporated by reference in its entirety herein. This application is also related to U.S. patent application Ser. No. 12/848,631, filed Aug. 2, 2010, now U.S. Pat. No. 8,141,875, issued Mar. 27, 2012, U.S. patent application Ser. No. 13/422,167, filed Mar. 16, 2012, and U.S. patent application Ser. No. 13/431,757, filed Mar. 27, 2012. This application is also related to U.S. patent application Ser. No. 13/714,211, filed Dec. 13, 2012.

FIELD OF THE INVENTION

Embodiments of the present invention relate generally to the field of gaming and the field of casino table card gaming. More particularly, embodiments of the invention relate to the use of equipment for the delivery of playing cards.

BACKGROUND

Wagering games based on the outcome of randomly generated arrangements of cards are well known. Such games are widely played in gaming establishments and, often, a single deck of 52 playing cards is used to play the game. Some games use multiple decks of cards (typically six or eight decks), such as blackjack and baccarat. Other games use two decks of cards, such as double deck blackjack. Many specialty games use single decks of cards, with or without jokers and with or without selected cards removed. Examples of such games include THREE CARD POKER®, LET IT RIDE®, CARIBBEAN STUD POKER®, SPANISH 21®, FOUR CARD POKER®, CRAZY 4 POKER® and others. As new games are developed, card shufflers are modified to be used in connection with the new games.

From the perspective of players, the time the dealer must spend in shuffling diminishes the excitement of the game. From the perspective of casinos, shuffling time reduces the number of hands played and specifically reduces the number of wagers placed and resolved in a given amount of time, consequently reducing casino revenue. Casinos would like to increase the amount of revenue generated by a game without changing the game or adding more tables. One approach is to simply speed up play. One option to increase the speed of play is to decrease the time the dealer spends shuffling.

The desire to decrease shuffling time has led to the development of mechanical and electromechanical card shuffling devices. Such devices increase the speed of shuffling and dealing, thereby increasing actual playing time. Such devices also add to the excitement of a game by reducing the amount of time the dealer or house has to spend in preparing to play the game.

Dealers appreciate using card shufflers that place the minimum strain on the dealer's hands, back and arms. Some existing shuffler designs put unnecessary strain on the muscles of the users. Dealers prefer shufflers that are low profile, especially when the shuffler dispenses cards into a game rather than shuffle batches of cards for shoe games.

Numerous approaches have been taken to the design of card shufflers. These approaches include random ejection designs (e.g., U.S. Pat. Nos. 6,959,925; 6,698,756; 6,299,167; 6,019,368; 5,676,372; and 5,584,483), stack separation and insertion (e.g., U.S. Pat. Nos. 5,683,085 and 5,944,310), interleaving designs (e.g., U.S. Pat. Nos. 5,275,411 and 5,695,189), for example, random insertion using a blade (U.S. Pat. No. 5,382,024) and designs that utilize multiple shuffling compartments.

One such example of a compartment shuffler is disclosed in U.S. Pat. No. 4,586,712 to Lorber et al. The automatic shuffling apparatus disclosed is designed to intermix multiple decks of cards under the programmed control of a computer. The apparatus is a carousel-type shuffler having a container, a storage device for storing shuffled playing cards, a removing device and an inserting device for intermixing the playing cards in the container, a dealing shoe and supplying means for supplying the shuffled playing cards from the storage device to the dealing shoe. The container includes multiple card-receiving compartments, each one capable of receiving a single card.

Another shuffler having mixing compartments arranged in a carousel is disclosed in U.S. Pat. No. 6,267,248 to Johnson et al. Cards are loaded into an infeed tray, fed sequentially past a card-reading sensor and are inserted into compartments within a carousel to either randomize or sort cards into a preselected order. The carousel moves in two directions during shuffling. U.S. Pat. No. 6,676,127 to Johnson et al. describes another variation of the shuffler, in which cards are inserted into and removed from a same side of the carousel, with the card infeed tray being located above the discard tray (see FIG. 3).

U.S. Pat. No. 3,897,954 to Erickson et al. discloses a device for delivering cards, one at a time, into one of a number vertically stacked card-shuffling compartments. A logic circuit is used to determine the sequence for determining the delivery location of a card. The card shuffler can be used to deal stacks of shuffled cards to a player.

U.S. Pat. No. 4,770,421 to Hoffman discloses a card-shuffling device including a card loading station with a conveyor belt. The belt moves the lowermost card in a stack onto a distribution elevator whereby a stack of cards is accumulated on the distribution elevator. Adjacent to the elevator is a vertical stack of mixing pockets. A microprocessor preprogrammed with a finite number of distribution schedules sends a sequence of signals to the elevator corresponding to heights called out in the schedule. Single cards are moved into the respective pocket at that height. The distribution schedule is either randomly selected or schedules are executed in sequence. When the microprocessor completes the execution of a single distribution cycle, the cards are removed a stack at a time and loaded into a second elevator. The second elevator delivers cards to an output reservoir.

U.S. Pat. No. 5,275,411 to Breeding discloses a machine for automatically shuffling and dealing hands of cards. Although this device does not shuffle cards by distributing cards to multiple compartments, the machine is the first of its kind to deliver randomly arranged hands of cards to a casino card game. A single deck of cards is shuffled and then cards are automatically dispensed into a hand-forming tray. The shuffler includes a deck-receiving zone, a carriage section for separating a deck into two deck portions, a sloped mechanism positioned between adjacent corners of the deck portions, and an apparatus for snapping the cards over the sloped mechanism to interleave the cards. The Breeding shuffler was originally designed to be used in connection with single deck poker style games such as LET IT RIDE® stud poker and a variant of pai gow poker marketed as WHO'S FIRST® Pai Gow Poker.

In an attempt to speed the rate of play of specialty table games equipped with a shuffler, the ACE® card shuffler as disclosed in U.S. Pat. Nos. 6,149,154, 6,588,750, 6,655,684 and 7,059,602 was developed. This shuffler operates at faster speeds than previously known shuffler devices described above, has fewer moving parts, and requires much shorter set up time than the prior designs. The shuffler includes a card infeed tray, a vertical stack of shuffling compartments and a card output tray. A first card moving mechanism advances cards individually from the infeed tray into a compartment. A processor randomly directs the placement of fed cards into the compartments, and an alignment of each compartment with the first card mover, forming random groups of cards within each compartment. Groups of cards are unloaded by a second card-moving mechanism into the output tray.

Another compartment shuffler capable of delivering randomly arranged hands of cards for use in casino card games is the ONE-2-SIX® shuffler (developed by Casino Austria Research & Development (CARD)). This shuffler is disclosed in U.S. Pat. Nos. 6,659,460 and 6,889,979. This shuffler is capable of delivering randomly arranged hands of cards when a first delivery end is attached, and is capable of delivering a continuous supply of cards from a shoe-type structure when a second delivery end is attached. Cards are fed from a feeder individually into compartments within a carousel to accomplish random ordering of cards.

Most of the shuffler designs mentioned above are high profile and require loading cards into the rear of the machine, and then removing cards from the front of the machine. The cards must be lifted over the top of the machine to return spent cards to the infeed tray, causing a dealer to lift his arm over the top of the machine at the conclusion of each round of play. Newer shuffler designs are flush-mounted into a gaming table surface. One such shuffler of this type is disclosed in U.S. Pat. No. 6,651,982.

One particular type of card shuffling device is referred to as a batch type shuffler. One characteristic of a (single or double deck) batch type shuffler is that when all of the cards are dispensed in a round of play, the remaining cards in the pack (one or two decks) are removed and then reinserted. In use, while the game is being dealt using a first deck, a second deck of cards is being randomized and arranged into groups. A discard rack is typically provided on the table so that cards removed from the game are staged in the rack while the other deck of cards is being processed. Following this procedure avoids the possibility that cards will be returned to the input tray and that the two decks will be intermingled. The use of two separate decks (one at a time) speeds game play because shuffling of a first deck occurs during play with a second deck.

Continuous shufflers, in contrast, are not unloaded at the end of a round of play. Spent cards are returned and inserted, and new cards dispensed without removing the entire set.

U.S. Pat. No. 6,959,925 to Sines discloses a single deck continuous card shuffler known in the trade as the POKER-ONE®. This shuffler avoids the alternating use of two different decks of cards during a specialty card game by providing a continuous supply of cards to a card game. Although this shuffler uses only one deck of cards, the shuffler does not verify that the correct number of cards (typically 52) are present prior to each shuffle, and consequently player cheating by inserting extra cards would go undetected.

Shufflers that communicate with network-based game systems have been described in the art. An example is described in U.S. Patent Publication No. 2003/0064798A1. A shuffler with an on board microprocessor and communication port communicates with a local processor and/or a central processor. The local or central processor may manage a game system.

Using these card-handling devices, there are still many variables that can affect a Casino's margin of profit, one of which is the accuracy of a dealer in settling bets during any game play. Each table game in a casino is designed with a certain house advantage. The payouts for any winning hand are pre-determined by the game developer based on rigorous math analysis. Although it is a requirement that a dealer must be able to recognize all winning hands (of all different card combinations) and pay out appropriate amounts, it is common that a dealer makes mistakes by either misreading a hand or paying the wrong amount to a player with a winning hand.

Therefore, there is a need for a shuffler that has all of the performance attributes of known shufflers and enables checking the accuracy of casino games by detecting, storing, and retrieving information about the composition of present and past hands of cards in a casino table game.

BRIEF SUMMARY OF THE INVENTION

The present invention, in various embodiments, comprises methods, devices, systems, and computer-readable media configured for detecting, storing, and retrieving information about the composition of present and past hands of cards dispensed in a casino table game.

An embodiment of the invention includes an apparatus that includes a card-handling device, a card recognition system, a control system, and a display. The card-handling device may be used for randomizing and dispensing cards during a casino table game play. The cards may be dispensed as a plurality of hands, each hand including one or more cards. The card recognition system identifies card information including a rank and a suit of each card while each card is under the control of the card-handling device. The control system includes one or more processors and a memory. The control system is configured to control the card-handling device and receive the card information for each card from the card recognition system. The control system is also configured to maintain a play history including a card composition of a plurality of rounds. The card composition includes card information for each hand of each round. Finally, the card information of at least one hand from at least one round of play is presented on the display.

Another embodiment of the invention comprises a system that includes: (1) a card-handling device, (2) an object recognition device, and (3) a table manager. The card-handling device may be used for randomizing and dispensing cards during a casino table game play wherein the cards may be dispensed as a plurality of hands, each hand including one or more cards. The card-handling device includes a card recognition system for recognizing card information including a rank and a suit of each card while each card is under control of the card-handling device. The system also includes one or more processors for receiving the card information for each card from the card recognition system and determining the cards in each hand of a current round. The object recognition device identifies at least one betting object indicating at least one active player position for the current round. The table manager includes a computer and a display and is configured to receive position information about the at least one active player position from the object recognition device. The table manager also receives the card information from within the card-handling device and analyzes the card information and the position information to display the card information for the at least one active player position. In other embodiments, card information is determined in a processor external to the card-handling device.

Yet another embodiment of the invention includes a method of providing cards during casino table game play. The method includes causing a card-handling device to substantially automatically generate a plurality of hands wherein each hand includes one or more cards. The method also includes identifying card information including a rank and a suit of each card as the card moves through the card-handling device. The method further includes maintaining a play history including a card composition for a plurality of rounds wherein the card composition of each round includes the cards in each hand of the round. Finally, the method includes displaying the card information of at least one hand from at least one round. The display may be mounted to the card-handling device or may be a separate system component.

Yet another embodiment of the invention includes a computer-readable medium including computer-executable instructions which, when executed on one or more computers, perform the method recited above.

BRIEF DESCRIPTION OF THE DRAWINGS

In the drawings:

FIG. 3 is a top plan view of the card-handling device shown in FIG. 1;

DETAILED DESCRIPTION OF THE INVENTION

Figure 1:
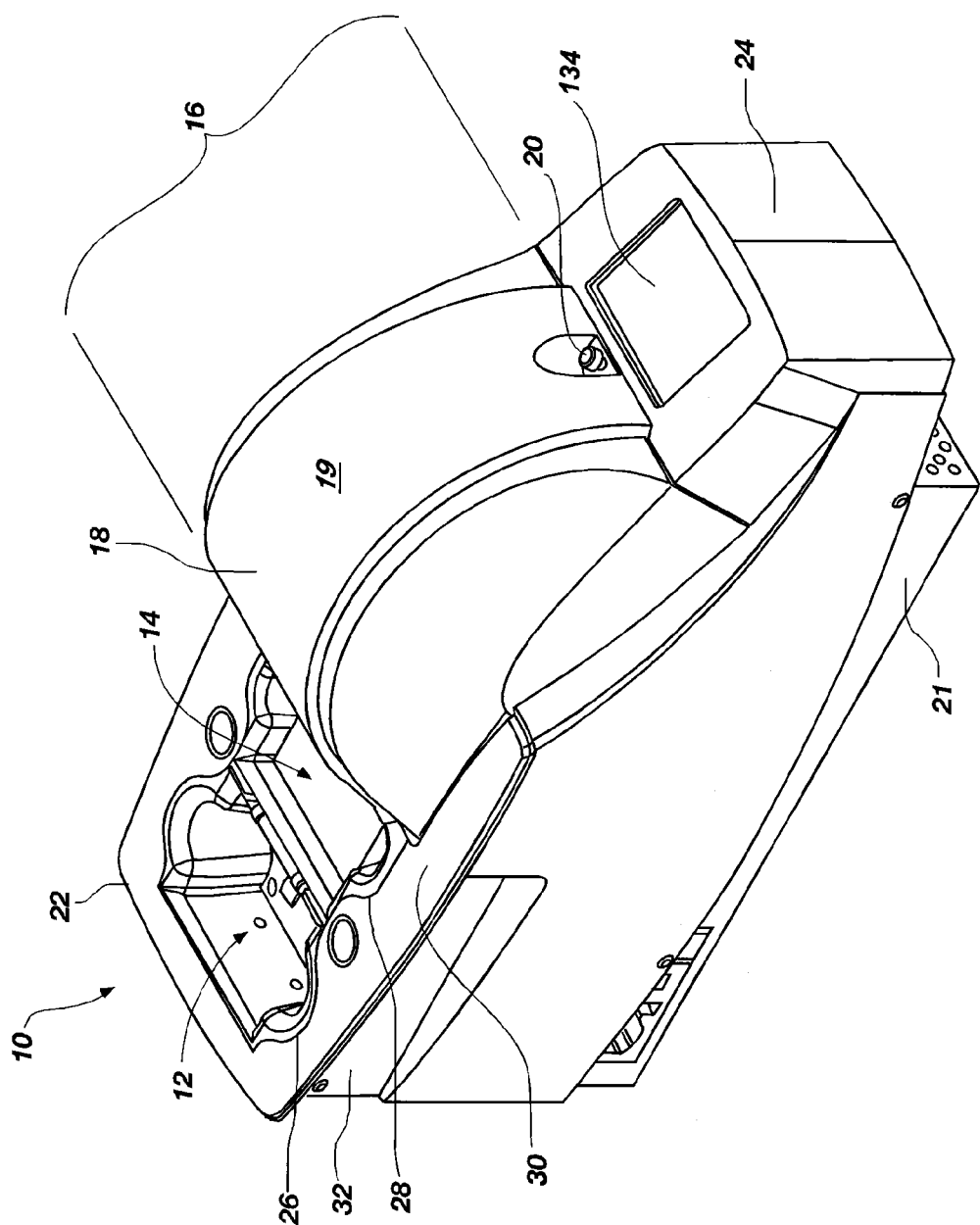
FIG. 1 is a perspective view of an embodiment of a card-handling device.

The present invention, in various embodiments, comprises methods, devices, and systems configured for detecting, storing, and retrieving information about the composition of present and past hands of cards in a casino table game.

The following provides a more detailed description of embodiments of the present invention. In this description, circuits and functions may be shown in block diagram form in order not to obscure the present invention in unnecessary detail. Conversely, specific implementations shown and described are exemplary only and should not be construed as the only way to implement the present invention unless specified otherwise herein. Additionally, block definitions and partitioning of functions between various blocks is exemplary of a specific implementation. It will be readily apparent to one of ordinary skill in the art that the present invention may be practiced by numerous other partitioning solutions.

Further, the term "module" is used herein in a non-limiting sense and solely to indicate functionality of particular circuits and assemblies included within embodiments of the invention, and may not be construed as requiring a particular physical structure, or particular partitioning between elements of the invention performing indicated functions.

In this description, some drawings may illustrate signals as a single signal for clarity of presentation and description. Persons of ordinary skill in the art will understand that the signal may represent a bus of signals, wherein the bus may have a variety of bit widths and the present invention may be implemented on any number of data signals including a single data signal.

Software processes illustrated herein are intended to illustrate representative processes that may be performed by the systems illustrated herein. Unless specified otherwise, the order in which the process acts are described is not intended to be construed as a limitation, and acts described as occurring sequentially may occur in a reverse sequence, or in one or more parallel process streams. Furthermore, the processes may be implemented in any suitable hardware, software, firmware, or combinations thereof.

When executed as firmware or software, the instructions for performing the processes may be stored on a computer-readable medium. A computer-readable medium includes, but is not limited to, magnetic and optical storage devices such as disk drives, magnetic tape, CDs (compact disks), DVDs (digital versatile discs or digital video discs), and semiconductor devices such as RAM, DRAM, ROM, EPROM, and Flash memory.

The disclosures of all patents, published patent applications, and other documents cited in this entire application are incorporated by reference in their respective entireties herein, whether or not such incorporation is specifically asserted in association with such citation.

Card-handling devices that embody teachings of the present invention may include major components that are physically arranged (for example, in a linear arrangement) in the following order: a) a playing card input compartment; b) a playing card retrieval compartment; and c) a playing card-handling zone. Playing cards may be moved from the playing card input compartment into the playing card-handling zone and from the playing card-handling zone into the playing card retrieval compartment. Furthermore, card-handling devices that embody teachings of the present invention may be configured to enable a user to either shuffle or selectively sort cards into a predefined order using the card-handling devices.

A perspective view of a card-handling device 10 according to embodiments of the present invention is shown in FIG. 1. The card-handling device 10 includes a card infeed tray 12, a card output tray 14, and a card-handling system or mechanism, which is described in further detail below. In some embodiments, the card output tray 14 may be removable for maintenance.

In some embodiments, the card infeed tray 12 and the card output tray 14 may be disposed adjacent one another. Furthermore, the card infeed tray 12 and the card output tray 14 each may be located near a first end 22 of the card-handling device 10. In some embodiments, the card infeed tray 12 and the card output tray 14 may each include a recessed area in the card-handling device 10, as shown in FIG. 1.

A major portion of the card-handling system may be located within a card-handling zone 16 of the card-handling device 10. The card-handling system may be enclosed within a cover 18, which, in this embodiment, has a curved upper surface 19 that is arched to enclose an upper portion of a carousel member (which is part of the card-handling system described in further detail below). The cover 18 may include a lock 20 to secure the cover 18 to a frame (not shown) of the card-handling device 10 to prevent unauthorized access to cards in the card-handling device 10. This locking feature advantageously allows a casino operator to shut down a table with cards loaded into the card-handling device 10. When the table is reopened, the operator can be assured that the cards held in the machine are secure. The key to the lock may be held by pit management, and the fact that the cover is, and has been, locked may eliminate any need to unload and verify the rank and suit of each card before play is resumed. Securing the cards within the card-handling device 10 when the machine is not in use is a valuable time and labor saving feature. The lock 20 may be located proximate a second end 24 of the card-handling device 10. Although an exemplary lock is a simple mechanical lock with rollers and a key, other locking systems may be used, such as, for example, electronic locks with keypad controls, locking systems that receive radio frequency identification (RFID) signatures, and computer-controlled locks.

Figure 2:
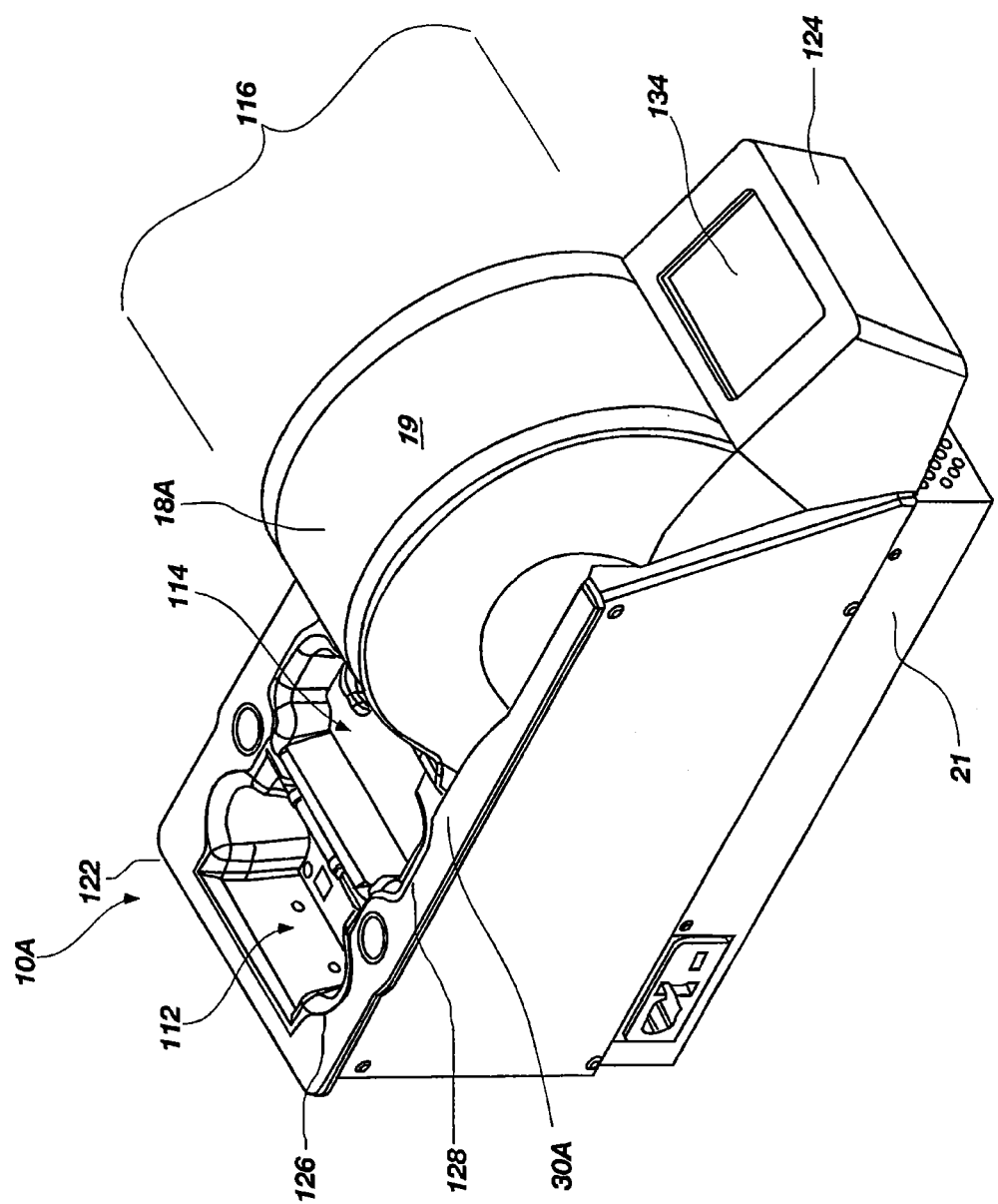
FIG. 2 is a perspective view of another embodiment of a card-handling device.

Additional card-handling devices according to embodiments of the present invention may not include an outer cover that is intended to be opened or removed by a user. For example, FIG. 2 illustrates another card-handling device 10A according to embodiments of the present invention that includes an outer cover 18A that is not intended to be opened or removed by a user. The card-handling device 10A may be otherwise substantially similar to the card-handling device 10, and may include a card infeed compartment 112, a card delivery compartment 114 near a first end 122 of the card-handling device 10A, and a card-handling zone 116 and a display 134 near a second end 124 of the card-handling device 10A. A card-handling mechanism comprising a carousel (not shown) is enclosed within the outer cover 18A. The outer cover 18A may be secured to the frame 21 and may be removable for maintenance, but may not be configured for removal by a user. In some embodiments, the outer cover 18A may be secured to the frame 21 with sheet metal screws. The card-handling device 10A may further include a flange 30A that intersects an upper edge 126 of the card infeed compartment 112 and an upper edge 128 of the card delivery compartment 114 and extends a portion of the way through the card-handling zone 116. This flange 30A may be mounted on a gaming table surface such that a portion of the card-handling zone 116 is positioned within the outside perimeter of the gaming table. A display 134 may be positioned at an elevation below the gaming table surface when the card-handling device 10A is mounted on or in a gaming table. The card-handling device 10A may be supported by the flange 30A, a table extension (not shown), a pedestal, a combination of the above, or by any other support technique.

Referring back to FIG. 1, the card infeed tray 12 and the card output tray 14 may be surrounded by a substantially flat flange 30 that intersects the upper edge 26 of the card infeed tray 12 and the upper edge 28 of the card output tray 14. In this configuration, the flat flange 30, the upper edge 26 of the card infeed tray 12, and the upper edge 28 of the card output tray 14 may be disposed in substantially the same plane. In other words, the upper edge 26 of the card infeed tray 12 and the upper edge 28 of the card output tray 14 may be substantially co-planar. In such a configuration, the card-handling device 10 may be mounted for use on or in a gaming table such that the flat flange 30, the upper edge 26 of the card infeed tray 12, and the upper edge 28 of the card output tray 14 are substantially flush with the upper surface of the gaming table.

In one mounting arrangement, a gaming table surface may be provided with a notch cut into an edge of the table facing the dealer. The first end 22 of the card-handling device 10 may include a recess 32 that has a size and shape that is configured to receive the side of the table therein along the notch. The remainder of the card-handling device 10 (e.g., the second end 24 of the card-handling device 10) may be supported by a support bracket beneath the table surface. In this configuration, the portion of the card-handling device 10 that is inserted into the gaming table may be flush mounted with the upper surface of the table.

In the arrangement described above, the first end 22 of the card-handling device 10 may be nearest the players and the second end 24 of the card-handling device 10 may be nearest the pit when the card-handling device 10 is mounted on or in a gaming table. Furthermore, the card-handling zone 16 may be located behind or to the side of the dealer and out of the way when the card-handling device 10 is mounted on or in the gaming table.

Because the card infeed tray 12 and the card output tray 14 are located on the same side of the card-handling zone 16 (near the first end 22 of the card-handling device 10), the cards may be more accessible to the dealer, and the dealer need not lift cards over the card-handling zone 16 to place spent cards back into the card-handling zone 16. The present design, therefore, may be relatively more ergonomically beneficial to the user (dealer) than known designs. Positioning the card infeed tray 12 at the table level also may reduce the possibility that card faces will be accidentally shown to players.

The placement of an upper edge 26 of the card infeed tray 12 and an upper edge 28 of the output tray 14 substantially in the same plane lying on, or proximate to, the gaming surface also may provide distinct ergonometric advantages. If the dealer moves his or her hands smaller distances during card handling, he or she is likely to experience fewer repetitive stress or strain injuries. Therefore, delivering spent cards to the card-handling device 10 at the gaming surface and retrieving freshly handled cards from substantially the same location or nearby offers distinct user advantages.

The placement of the infeed tray 12 and the output tray 14 on the same side of a carousel-type playing card-handling zone (discussed in further detail below) also allows the user to place spent cards-face down in the infeed tray 12, and at the same time receive fresh cards from the output tray 14 in a face-down configuration. This attribute has been previously described in U.S. Pat. No. 6,676,127 to Johnson et al. This feature improves the security of a carousel card-handling device 10, since no cards are exposed during loading, shuffling, or unloading.

A horizontally disposed centerline intersecting the card infeed tray 12 and the card output tray 14 may also advantageously intersect a centerline of the card-handling zone 16, as will be discussed in more detail below. This arrangement allows the machine to be fairly narrow in width and permits both card tray areas (but not the more bulky card-handling zone 16) to be located on or near the playing table surface.

The card-handling zone 16 of the card-handling device 10 may include card-moving elements located below the card infeed and output trays. The card-handling zone 16 may be capable of performing at least one of the following functions: a) shuffling, b) arranging cards into a desired order, c) verifying completeness of a group of cards, d) reading special markings on cards (such as, for example, a casino identification mark, a manufacturer identification mark, a special bonus card identification mark, a deck identification mark, etc.), e) scanning cards for unauthorized markings, f) identifying cards lacking required markings, g) measuring card wear, h) decommissioning cards, i) applying markings to cards, j) scanning cards for unauthorized electronic devices, k) delivering special cards such as, for example, bonus cards, promotional cards, or wild cards, and many other useful functions.

In some embodiments of the present invention, the card-handling zone 16 may comprise a card-handling system or mechanism comprising a temporary card storage device or system 244 (FIG. 8), a card infeed mechanism or system 240 (FIG. 8) for moving cards from the card infeed tray 12 to the temporary card storage system 244 (FIG. 8), and a card output mechanism or system 242 (FIG. 8) for moving cards from the temporary card storage system 244 (FIG. 8) to the card output tray 14. In some embodiments of the present invention, the temporary card storage system 244 (FIG. 8) may comprise a carousel device having multiple compartments for receiving cards therein, as discussed in further detail below. Many types of card-handling systems or mechanisms that include other types of temporary card storage devices may be utilized in card-handling devices that embody teachings of the present invention. Some non-limiting examples of such other types of card-handling systems or mechanisms include the card-handling system described in detail in U.S. Pat. No. 6,959,925 to Baker et al., the vertical compartment card-handling system described in U.S. Pat. No. 6,149,154 to Grauzer et al., and the card-handling system described in U.S. Pat. No. 6,651,981 to Grauzer et al.

FIG. 3 is a top plan view of the card-handling device 10 shown in FIG. 1. The card infeed tray 12 and the card output tray 14 may be positioned on the same side of the card-handling device 10 and in substantially a common plane. For example, the card infeed tray 12 and the card output tray 14 each may be positioned proximate the first end 22 of the card-handling device 10. Furthermore, the card infeed tray 12 and the card output tray 14 each may be positioned on the same side of the card-handling zone 16 (which may include, for example, a carousel 120, as discussed in further detail below). In some embodiments of the present invention, the card infeed tray 12 and the card output tray 14 each may be bisected by a centrally located longitudinal axis 36. Furthermore, in some embodiments, the card infeed tray 12 and the card output tray 14 each may be substantially symmetrically bisected by the longitudinal axis 36. As also shown in FIG. 3, the card infeed tray 12 may be equipped with a gate member 98 whose functions will be described in more detail below. The card infeed tray 12 also may include a sensor 38 configured to detect the presence of any card provided in the card infeed tray 12.

Declining finger cut-outs 33A or recesses may be provided in the interior surfaces of the card infeed tray 12, and declining finger cut-outs 33B or recesses may be provided in the interior surfaces of the card output tray 14. The finger cut-outs 33A and 33B may have a size and shape configured to receive or accommodate at least one digit of the hand of a person therein to facilitate handling of cards in the card infeed tray 12 and the card output tray 14 by a user.

Figure 4A:
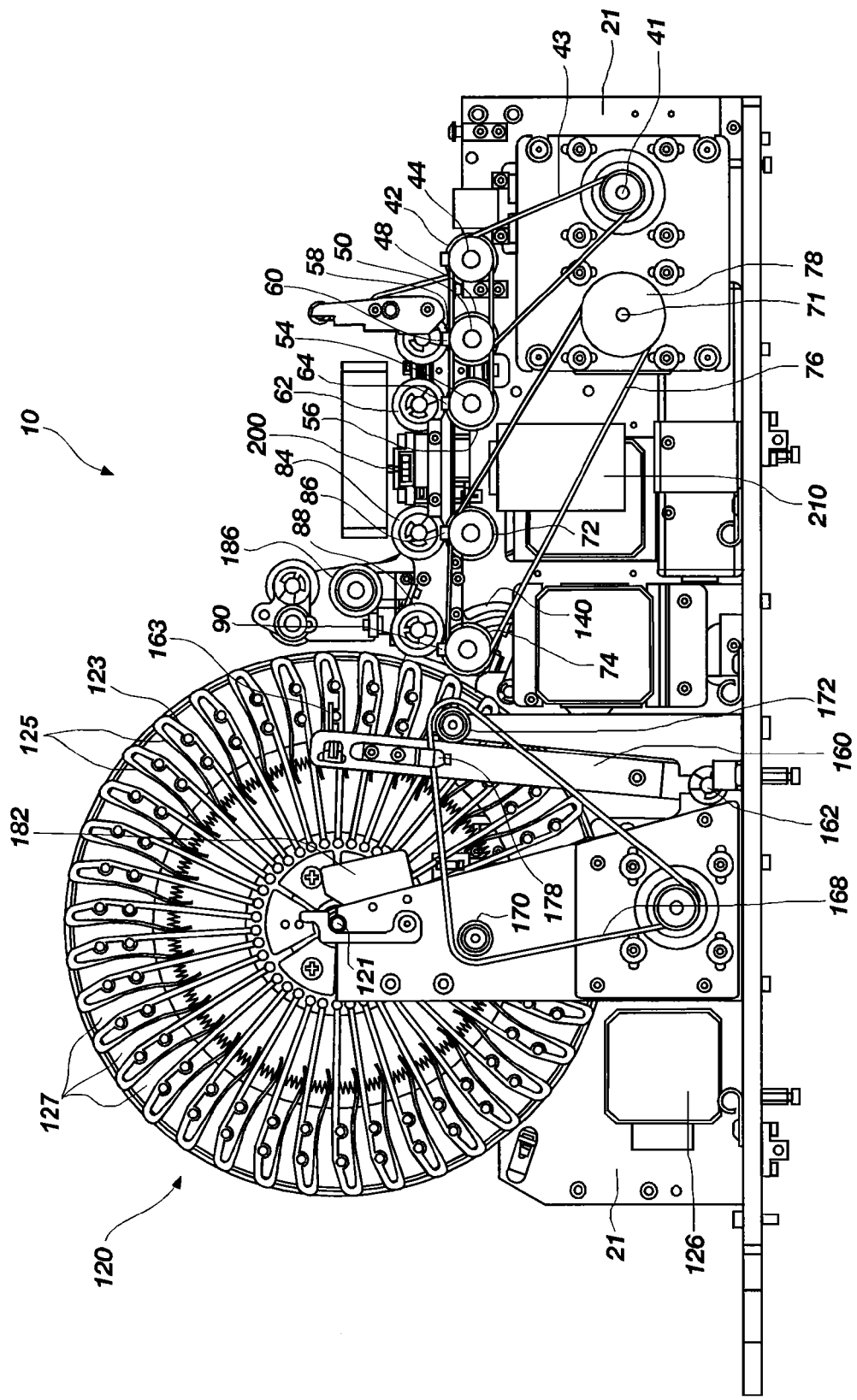
FIG. 4A is a view of a first side elevational view of the card-handling device shown in FIG. 1 with the cover removed to facilitate illustration of active components of the card-handling device.
Figure 4B:
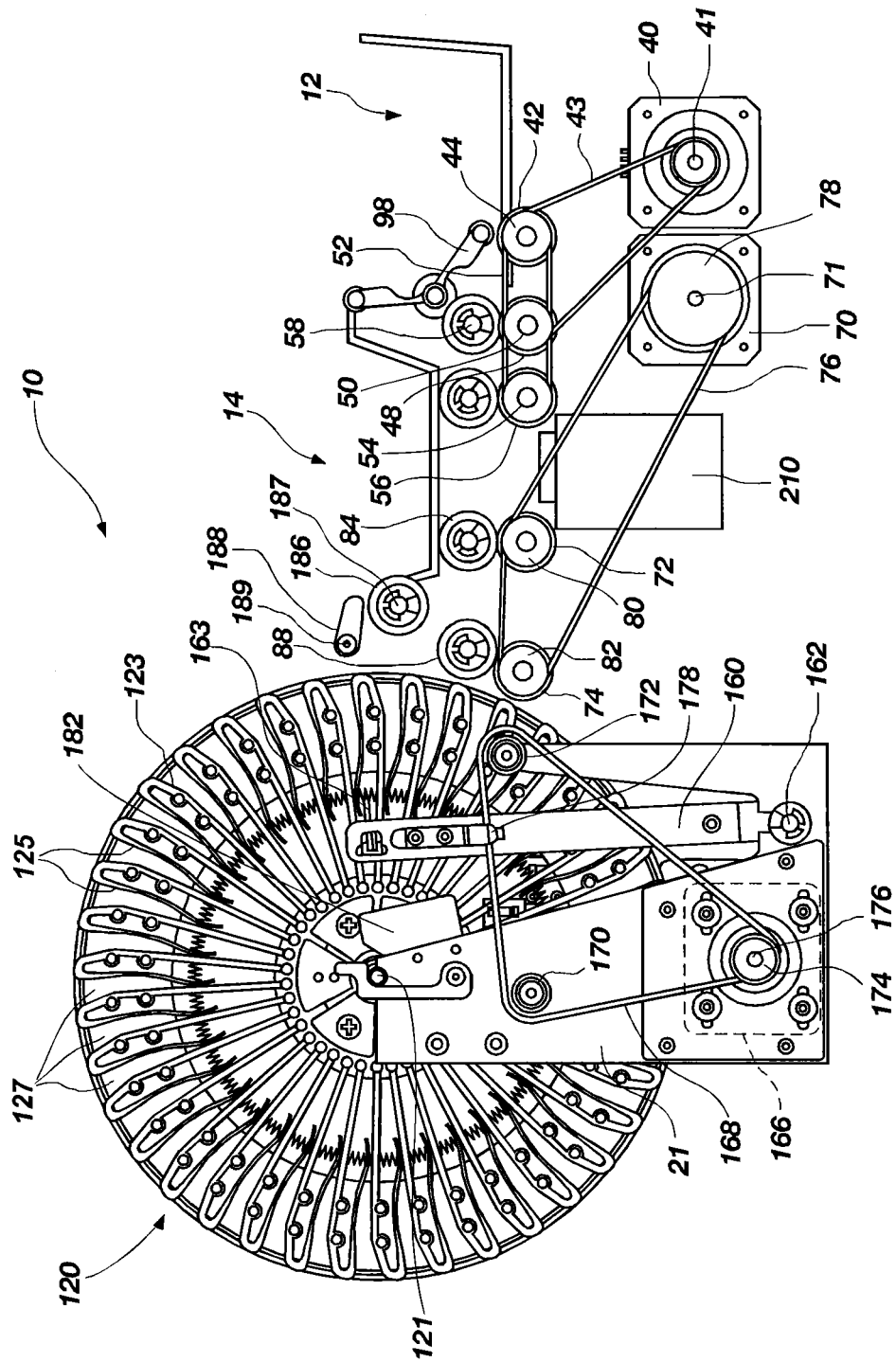
FIG. 4B is a simplified version of FIG. 4A, illustrating only selected elements to facilitate description of those elements.

FIG. 4A is a side view of the card-handling device 10 shown in FIG. 1 with the cover 18 removed. FIG. 4B is a simplified version of FIG. 4A, illustrating only certain elements of the card-handling device 10 to facilitate description thereof. Referring to FIGS. 4A and 4B in combination, the card-handling device 10 may include a card infeed system 240 (FIG. 8) comprising a first drive system and a second drive system.

The first drive system may include a first card infeed motor 40 (FIG. 4B) that is configured to drive rotation of a card feed roller 42 using a first endless toothed belt 43 coupled to both a drive sprocket 44, which is mounted on a drive shaft 41 of the motor 40, and the card feed roller 42. A lowermost card in a stack of spent cards placed in the card infeed tray 12 will come into contact with card feed roller 42. The first card infeed motor 40 is also configured to rotationally drive a first advancing roller 48 using the first endless toothed belt 43. A second endless toothed belt 52 meshes with a sprocket 50 as well as a sprocket 54 on a shaft carrying a second advancing roller 56. In this configuration, as the first card infeed motor 40 drives rotation of the card feed roller 42 and the first advancing roller 48 with the first endless toothed belt 43, the first card infeed motor 40 will also drive rotation of a second advancing roller 56 with a second endless toothed belt 52. First opposing idler roller 58 adjacent the first advancing roller 48 forms a first nip 60 (FIG. 4A), and second opposing idler roller 62 adjacent roller 56 forms a second nip 64 (FIG. 4B). The first opposing idler roller 58 may be adjustable in the vertical direction of FIG. 4A. Cards provided in the card infeed tray 12 (FIG. 4B) may be sequentially moved in the horizontal direction of FIGS. 4A and 4B by the card feed roller 42 into the first nip 60, and subsequently into the second nip 64.

The second drive system may include a second card infeed motor 70 (FIG. 4B) that is configured to drive rotation of a third advancing roller 72 and a fourth advancing roller 74 using a third endless toothed belt 76 that is coupled to a pulley 78 mounted on a drive shaft 71 of the motor 70, a pulley 80 mounted on a shaft carrying the third advancing roller 72, and a pulley 82 mounted on a shaft carrying the fourth advancing roller 74. A third opposing idler roller 84 adjacent the third advancing roller 72 forms a third nip 86 (FIG. 4A), and a fourth opposing idler roller 88 adjacent roller 74 forms a fourth nip 90 (FIG. 4B). The fourth opposing idler roller 88 and the fourth nip 90 may be oriented and configured to deflect a card passing therebetween upwardly and into a compartment 127 or other card storage area of a carousel 120 or other temporary card storage device.

The first card infeed motor 40 and the second card infeed motor 70 each may be operatively controlled by a control system 220 (FIG. 8), which is described in further detail below.

In additional embodiments of the present invention, the card infeed system 240 (FIG. 8) may include only one motor, or more than two motors. Additionally, the card infeed system 240 (FIG. 8) may include any number of advancing rollers and corresponding idler rollers. Furthermore, any means for rotationally driving the card feed roller 42 and the advancing rollers 48, 56, 72, 74 may be used including, for example, gears, sprockets, chains, belts, etc. In yet additional embodiments, the card feed roller 42 and each of the advancing rollers 48, 56, 72, 74 may be directly mounted on a drive shaft of a corresponding motor.

Figure 5:
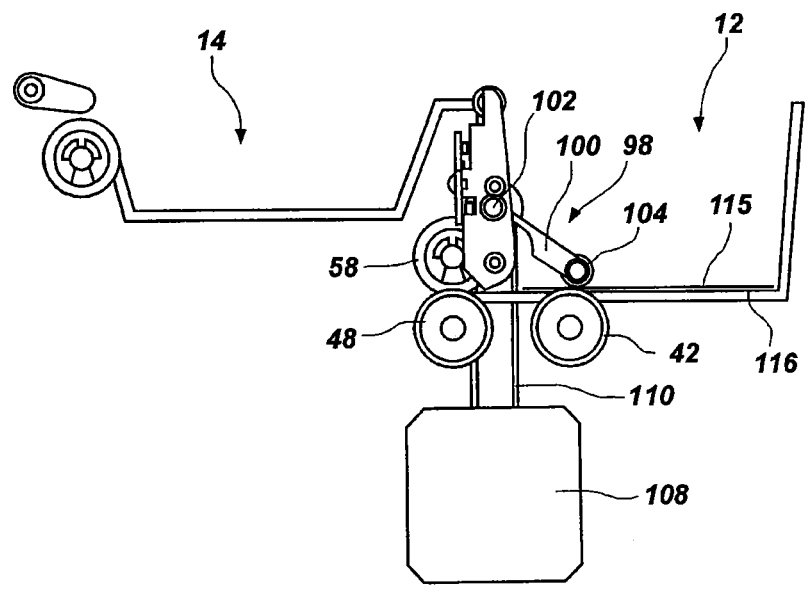
FIG. 5 is an enlarged partial side view of a card infeed tray, card feed roller, and dual function gate of the card-handling device shown in FIG. 1.

Referring to FIG. 5, in some embodiments of the present invention, the card infeed system 240 (FIG. 8) of the card-handling device 10 may further include a gate member 98 operatively associated with the card infeed tray 12. The gate member 98 may comprise an extension arm 100 having a first end that is connected to a shaft 102. The shaft 102 may be rotationally driven by an infeed gate motor 108 and an endless belt 110. A roller 104 may extend substantially transversely from the extension arm 100 (i.e., into the plane of FIG. 5), and may be used to reduce frictional contact with cards 115 in the card infeed tray 12. The roller 104 may be rotationally coupled to the second end of the extension arm 100, and may extend substantially across a width of any cards 115 in the card infeed tray 12 (or a length of any cards 115 in the card infeed tray 12, depending on the orientation of the cards 115 in the card infeed tray 12). In this configuration, the extension arm 100 will pivot about the shaft 102 as the infeed gate motor 108 drives rotation of the shaft 102 using the endless belt 110. The extension arm 100 and roller 104 may be positioned in an upright and retracted pivotal position (not shown) in which the roller 104 does not engage any cards 115 in the card infeed tray 12, to a downwardly angled engaged position in which the roller 104 engages and abuts against the cards 115 in the card infeed tray 12.

Figure 8:
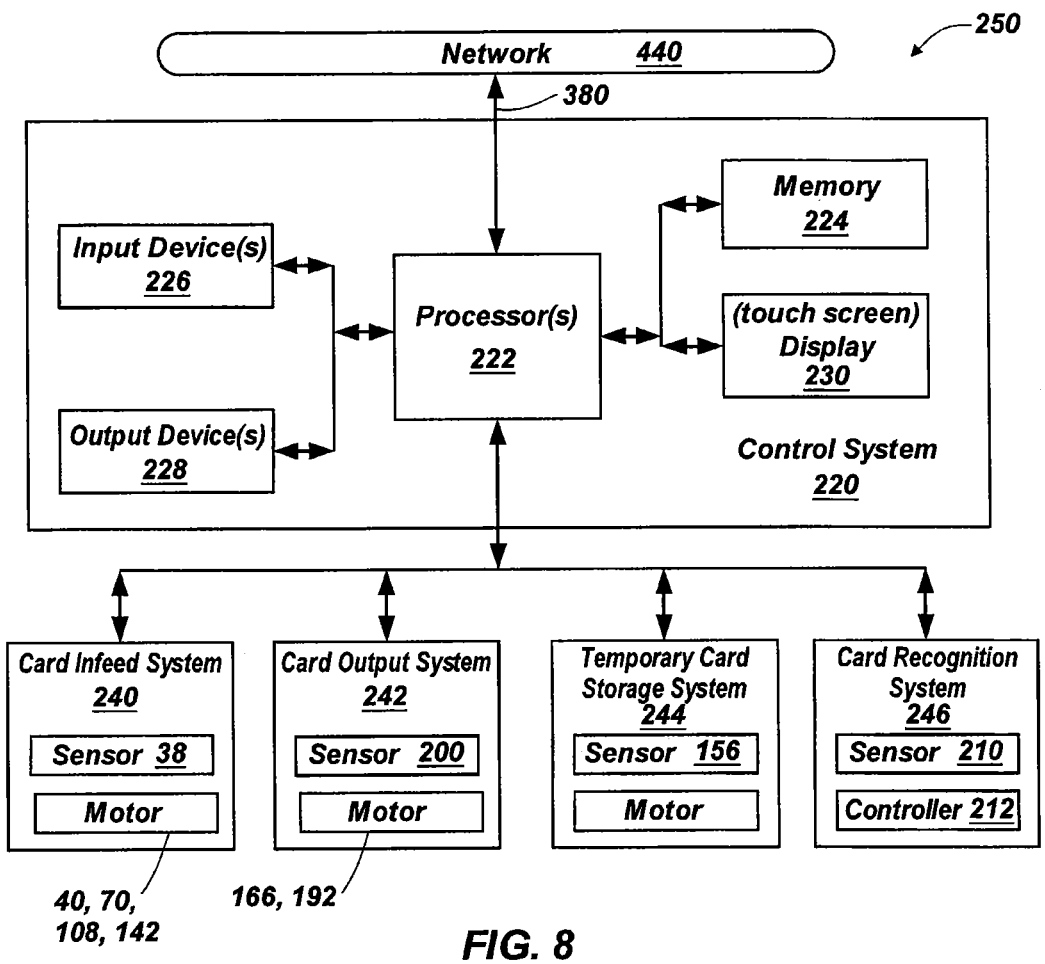
FIG. 8 is a schematic diagram of a control system that may be used in card-handling devices that embody teachings of the present invention, such as that shown in FIG. 1.

The gate member 98 may serve a number of functions. For example, as the number of cards 115 in the card infeed tray 12 is reduced, the weight of the stack of cards 115 in the card infeed tray 12 is reduced, which may reduce the frictional force between the lowermost card 115 in the card infeed tray 12 and the card feed roller 42. The reduced frictional force between the lowermost card 115 in the card infeed tray 12 and the card feed roller 42 may impair the ability of the card feed roller 42 to move the lowermost card 115 to the first advancing roller 48 and to other elements of the card infeed system 240 (FIG. 8). Therefore, the gate member 98 may be used to apply a downward force to the cards 115 in the card infeed tray 12 to maintain the frictional force between the lowermost card 115 in the card infeed tray 12 and the card feed roller 42 above a threshold level. In some embodiments, the gate member 98 may be used to apply a downward force to the cards 115 in the card infeed tray 12 that increases as the number of remaining cards 115 decreases to provide a substantially constant force to the lowest card 115 in the card infeed tray 12. In other words, the gate member 98 provides additional weight against the cards 115 in the card infeed tray 12, which may improve the reliability by which the cards 115 in the card infeed tray 12 are taken into the first nip 60 (FIG. 4A) by the card feed roller 42.

The gate member 98 also may be used to provide a physical separation barrier between cards 115 in the card infeed tray 12 belonging or corresponding to different decks, or between different types of cards (such as regular cards and bonus cards, for example). When the card infeed system 240 (FIG. 8) of the card-handling device 10 is actively moving cards 115 from the card infeed tray 12 to the carousel 120 or other card storage device, the gate member 98 may be in the previously described downwardly engaged position. At the same time, the dealer may be collecting spent cards 115 from the playing table. Because the gate is in the downwardly engaged position, the dealer may put the spent cards (which may correspond to a first deck) in the card infeed tray 12 on top of or over at least a portion of the gate member 98, while the cards previously placed in the card infeed tray 12 (which may correspond to a second, different deck) are being moved from the card infeed tray 12 to the carousel 120 by the card infeed system 240 (FIG. 8). Therefore, in some embodiments of the present invention, a dealer or other user may load cards 115 from a first deck into the card infeed tray 12 while at least some cards 115 from a second deck remain in the card infeed tray 12 without causing or allowing the card-handling device 10 to mix cards from the first deck with cards from the second deck. As a result, the use of the gate member 98 may permit a casino to eliminate use of discard racks (which are typically mounted on gaming table surfaces for holding spent cards until they can be fed into a card-handling device), as spent cards may be placed without delay directly into the card infeed tray 12.

Once the last of the cards 115 below the gate member 98 in the card infeed tray 12 has been removed from the card infeed tray 12 by the card infeed system 240 (FIG. 8), the gate member 98 may be caused to rotate about the shaft 102 to the previously described retracted position to allow any cards 115 previously placed over the gate member 98 in the card infeed tray 12 to fall to the bottom of the card infeed tray 12 adjacent the card feed roller 42. In the retracted position, the gate member 98 may not obstruct the user from inserting additional cards 115 into the card infeed tray 12.

The shaft 102 may be located a selected distance below the upper edge 26 of the card infeed tray 12 (FIG. 1) so that the roller 104 does not extend substantially above the upper edge 26 of the card infeed tray 12 when the gate member 98 is in the previously described retracted position. Furthermore, the shaft 102 may be located a selected distance above the bottom surface 116 of the card infeed tray 12 to enable at least one entire deck of cards 115 to be received in the card infeed tray 12 and allow the roller 104 to abut against the top card 115 in the at least one entire deck of cards 115. Furthermore, the extension arm 100 may have a selected length to provide a distance between the rotational axis of the shaft 102 and the rotational axis of the roller 104 that is short enough that cards 115 provided over the gate member 98 in the card infeed tray 12 will lift and fall to the bottom of the card infeed tray 12 without flipping over as the gate member 98 pivots upwardly in the counterclockwise direction of FIG. 5. A currently preferred gate length is about one-third the length of the cards 115 (or the width of the cards 115, depending on the orientation of the cards 115 in the card infeed tray 12.

The infeed gate motor 108, which is used to selectively rotate the gate member 98, may be operatively controlled by a control system 220, which is described in further detail below.

Referring again to FIG. 4A, the card infeed system 240 (FIG. 8) of the card-handling device 10 may further include a packer arm device 140 for assisting the insertion of a card into a compartment 127 of the carousel 120 or other card storage device. As shown in FIGS. 4A and 4B, each compartment 127 of the carousel 120 may include a leaf spring member 125. As a result, the force of each leaf spring member 125 may need to be overcome as a card is inserted into each compartment 127. The packer arm device 140 may be used to provide additional force to the card as it leaves the fourth advancing roller 74 and corresponding opposing idler roller 88 and enters a compartment 127 of the carousel 120.

Figure 6:
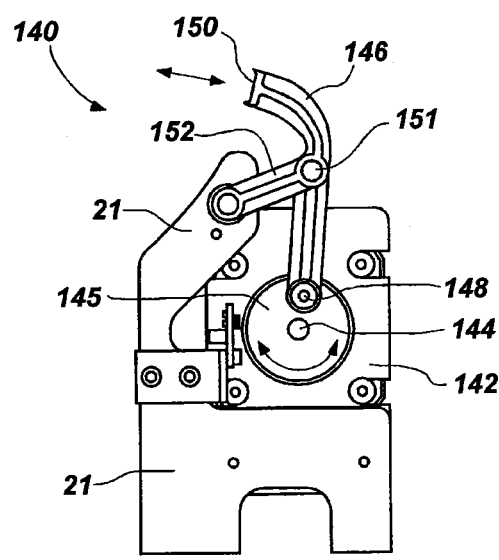
FIG. 6 is an enlarged detailed view of a packer arm assembly of the card-handling device shown in FIG. 1.

FIG. 6 is an enlarged stand-alone view of one embodiment of a packer arm device 140 that may be used in card-handling devices that embody teachings of the present invention, such as the card-handling device 10. As shown in FIG. 6, the packer arm device 140 may include a packer arm motor 142, which may be mounted to the frame 21 of the card-handling device 10. The packer arm motor 142 may be configured to rotate a shaft 144. An eccentric cam member 145 may be mounted to the shaft 144. An elongated packer arm 146 configured as a lever member may be pivotally coupled at a first end 148 thereof to the eccentric cam member 145. The packer arm 146 also may be pivotally attached to a first end of a pivot arm member 152 at an intermediate location 151 along the packer arm 146 between the first end 148 and a second end 150 thereof. A second end of the pivot arm member may be pivotally attached to a frame 21 of the card-handling device 10 or another stationary element of the card-handling device 10.

In this configuration, as the packer arm motor 142 drives rotation of the shaft 144 and eccentric cam member 145 in the direction indicated by the directional arrows shown on the eccentric cam member 145 in FIG. 6, the second end 150 of the elongated packer arm 146 may rock back and forth along an arc-shaped path in the directions indicated by the directional arrows shown proximate the second end 150 of the elongated packer arm 146 in FIG. 6.

The packer arm device 140 may be located in the card-handling device 10 such that the second end 150 of the elongated packer arm will abut against a trailing edge of a card and force the card completely into an aligned compartment 127 of the carousel 120. As the eccentric cam member 145 continues to rotate, the second end 150 of the elongated packer arm 146 may retract to a position that will allow a subsequent card to move past the packer arm device and into position for insertion into a compartment 127 of the carousel 120. In some embodiments of the present invention, the subsequently described control system 220 may cause the packer arm 146 to retract while the carousel 120 is rotating and to extend when the carousel 120 is stationary.

The packer arm motor 142, which is used to selectively move the packer arm 146, also may be operatively controlled by a control system 220, which is described in further detail below.

Referring again to FIG. 4A, as previously discussed, the carousel 120 may include a plurality of compartments 127, each of which may include a leaf spring 125 for holding cards securely within the compartment 127 after insertion. In this configuration, the cards may remain secured within the compartments 127 as the carousel 120 rotates in either the clockwise or counterclockwise direction of FIG. 4A. Each compartment 127 also may have at least one beveled surface 123 for deflecting cards into the aligned compartment 127 during insertion. In some embodiments of the present invention, the compartments 127 of the carousel 120 may be substantially equally sized, and each may be capable of holding up to ten conventional playing cards. By way of example and not limitation, the carousel 120 may include thirty-eight (38) compartments 127. In additional embodiments, the carousel 120 may include fewer than thirty-eight (38) compartments 127 or more than thirty-eight (38) compartments 127.

In some embodiments of the present invention, the previously described card infeed system 240 (FIG. 8) may be capable of selectively inserting a card into a compartment 127 of the carousel 120 either below or above any cards previously inserted and still disposed within that respective compartment. For example, each compartment 127 may have two corresponding card insertion rotational positions of the carousel 120. When the carousel 120 is rotationally positioned in the first of the card insertion rotational positions, any card inserted into the compartment 127 may be inserted below or under any cards previously inserted and still disposed within that respective compartment. When the carousel 120 is rotationally positioned in the second of the card insertion rotational positions, however, any card inserted into the compartment 127 may be inserted above or over any cards previously inserted and still disposed within that respective compartment.

The path that is traveled by a card as it moves from the card infeed tray 12 to a compartment 127 of the carousel 120 is substantially straight and substantially horizontal. In this configuration, the distance traveled by the cards along the path is the shortest distance between the cards in the card infeed tray 12 and the compartment 127 of the carousel 120. The length of this path traveled by the cards may be minimized to minimize the length of the card-handling device 10, and to maximize the speed by which cards may be delivered from the card infeed tray 12 to the carousel 120.

When the card-handling device 10 is mounted on a gaming table such that the flange 30 is substantially flush with the upper gaming surface of the table, approximately the lower half of the carousel 120 may be located beneath the table surface. As a result, the card-handling device 10 may have a relatively low profile on the table.

With continued reference to FIG. 4A, the card-handling device 10 may further include a carousel drive system configured to selectively drive rotation of the carousel member about a shaft 121, by which the carousel 120 is rotatably mounted to the frame 21. The shaft 121 may be mounted to the frame 21 by means of threaded hand screws or a locking releasable mechanism, which may provide for easy removal and replacement of the carousel 120.

Figure 7:
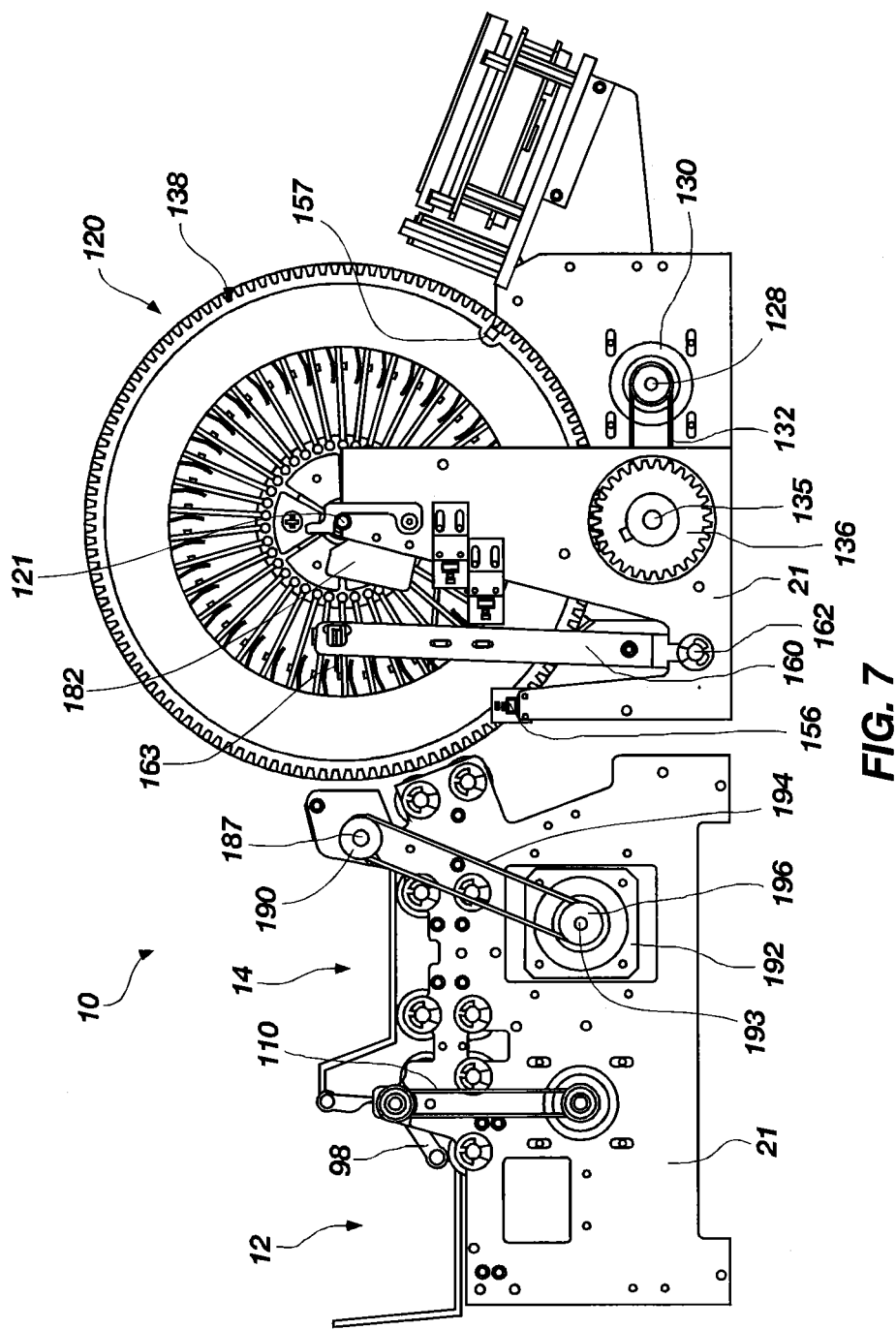
FIG. 7 is a view of a second, opposite side elevational view of the card-handling device shown in FIG. 4A.

The carousel drive system may include, for example, a carousel drive motor 126 that is mounted to the frame 21, as shown in FIG. 4A. FIG. 7 is a view of a second, opposite side of the card-handling device shown in FIG. 4A. By way of example and not limitation, a pulley 130 may be mounted to a drive shaft 128 of the carousel drive motor 126 (FIG. 4A), and another pulley (not shown) may be mounted to a drive shaft 135. An endless belt 132 may be provided around both the pulley 130 and the pulley mounted to the drive shaft 135. In this configuration, as the carousel drive motor 126 drives rotation of the drive shaft 128, the drive shaft 135 will also be rotationally driven by the carousel drive motor 126 and endless belt 132. A pinion gear 136 also may be mounted to the drive shaft 135. The pinion gear 136 may be sized, positioned, and otherwise configured to mesh with a toothed edge or surface 138 provided on the carousel 120. In this configuration, the carousel drive motor 126 may be used to selectively drive rotation of the carousel 120 about the shaft 121 in either the clockwise or counterclockwise direction.

In additional embodiments of the present invention, the carousel drive system may include any means for driving rotation of the carousel 120 including, for example, gears, sprockets, chains, belts, etc.

The carousel drive motor 126, which is used to selectively drive rotation of the carousel 120, also may be operatively controlled by a control system 220, which is described in further detail below.

Referring again to FIG. 4A, the card-handling device 10 may further include a card output system 242 (FIG. 8) for moving cards out from the carousel 120 or other card storage device and into the card output tray 14. The card output system 242 (FIG. 8) may include, for example, an elongated swing arm 160 having a first lower end that is pivotally coupled to the frame 21 using a pin member 162. The swing arm 160 may be configured to pivot about the pin member 162. The second upper end of the elongated swing arm 160 may be equipped or otherwise provide with a retractable inwardly projecting tab 163 (extending into the plane of FIG. 4A) that is configured to extend into a compartment 127 of the carousel 120 while the swing arm 160 is swinging toward the output tray 14, but that retracts before and/or while the swing arm 160 swings back to a resting position in which the swing arm 160 is positioned near an inner circumference 164 of the compartments 127 of the carousel 120. In the extended position, the inwardly projecting tab 163 contacts any cards positioned within the aligned compartment 127 of the carousel 120. The inwardly projecting tab 163 of the swing arm 160 retracts as it comes into contact with a stationary tab 182 mounted to the frame 21.

Referring to FIG. 4B, the card-handling device 10 may include a swing arm drive system, which may include a swing arm drive motor 166, an endless belt 168, a first idler pulley 170, and a second idler pulley 172. The first idler pulley 170 and the second idler pulley 172 may be mounted to the frame 21. The endless belt 168 may extend around a pulley 174 that is mounted to a drive shaft 176 of the swing arm drive motor 166, the first idler pulley 170, and the second idler pulley 172. The endless belt 168 is also securely attached to the swing arm 160 at a location between the first idler pulley 170 and the second idler pulley 172 using, for example, a clamp 178. In this configuration, the swing arm 160 may be selectively swung towards the card output tray 14 by selectively jogging the endless belt 168 around the pulleys 170, 172, 174 in the clockwise direction in FIG. 4B using the swing arm drive motor 166, and the swing arm 160 may be selectively swung away from the card output tray 14 by selectively jogging the endless belt 168 around the pulleys 170, 172, 174 in the counterclockwise direction in FIG. 4B using the swing arm drive motor 166.

The swing arm drive motor 166, which is used to selectively move the swing arm 160, also may be operatively controlled by the control system 220 subsequently described herein.

Referring to FIG. 4B, as the swing arm 160 is caused to swing towards the card output tray 14 and eject a card or cards out from a compartment 127 of the carousel 120, the card may be at least partially forced between a card output roller 186 and an opposing card output idler roller 188. The card output roller 186 may be mounted on a shaft 187. As shown in FIG. 7, a pulley 190 also may be mounted on the shaft 187, and a card output roller drive motor 192 that is attached to the frame 21 may be used to drive rotation of the shaft 187 using an endless belt 194. The endless belt 194 may extend around a pulley 190 mounted on the shaft 187 and another pulley 196 mounted on a drive shaft 193 of the card output roller drive motor 192. In some embodiments of the invention, intermeshing gears may be provided on both the shaft 187 of the card output roller 186 and a shaft 189 of the opposing card output idler roller 188 to ensure that the card output roller 186 and opposing card output idler roller 188 are driven in unison. In this configuration, the card output roller drive motor 192 may be caused to spin the card output roller 186 and opposing card output idler roller 188 as the swing arm 160 is caused to eject a card or cards out from a compartment 127 of the carousel 120 and force the card or cards between the card output roller 186 and the opposing card output idler roller 188. The rotation of the card output roller 186 and an opposing card output idler roller 188 may force and advance the card or cards therebetween into the card output tray 14, where the card or cards may be accessible to a dealer or other user of the card-handling device 10. A sensor 200 (FIG. 4A) may be located and configured to sense or detect when no cards are present in the card output tray 14, and to convey such information to the control system 220 subsequently described herein.

As shown in FIG. 7, one or more sensors 156 may also be provided and configured to detect a relative position of the carousel 120 so as to enable the control system 220 (FIG. 8) subsequently described herein to identify which compartment 127 is aligned to receive a card from the card infeed system 240 and which compartment 127 is aligned for ejection of any cards therein by the card output system 242. By way of example and not limitation, the card-handling device 10 may include one magnetic sensor 156 that is configured to detect a magnet 157 positioned on the carousel 120, as shown in FIG. 7. The position of the carousel 120 when the magnet 157 is positioned adjacent the magnetic sensor 156 may be designated as a "home" position of the carousel 120. The card-handling device 10 may be configured to position the carousel 120 in the home position when the card-handling device 10 is powered on. An encoder that is associated with at least one of the carousel drive motor 126 or the carousel 120 itself then may be used to keep track of the rotational movement of the carousel 120 from the home position, and the information received from the encoder may be used by the control system 220 (FIG. 8) to identify the relative rotational position of the carousel 120 at any given time.

In the embodiment described above, the path each card travels as the card moves from a selected compartment 127 of the carousel 120 into the card output tray 14 (i.e., the card output path) is substantially horizontal and above the path each card travels as the card moves from the card infeed tray 12 to a selected compartment 127 of the carousel 120 (i.e., the card infeed path). In additional embodiments of the present invention, the card infeed path may be positioned vertically above the card output path. This vertical stacking or layering of the card infeed path and the card output path allows both the card infeed tray 12 and the card output tray 12 to be positioned on the same side of the card-handling device 10 (relative to the carousel 120 or other card storage device). In yet additional embodiments, the card infeed path and the card output path may be disposed in substantially the same plane and laterally side by side one another.

Referring to FIGS. 4A and 4B, in embodiments of the present invention, the card-handling device 10 further includes a card sensing system (also referred to as a card recognition system) that is configured to sense at least one identifying characteristic or feature (also referred to as card information) of each card before the card is placed into a compartment 127 of the carousel 120 or other card storage device. By way of example and not limitation, the card recognition system may include a card sensor 210 that is configured to identify at least a rank (e.g., 2, 3, 4 . . . 10, jack, queen, king, ace) and suit (e.g., spade, club, diamond, heart) of a conventional playing card. The sensor 210 may be configured and positioned, for example, to detect the rank and suit of each card as the card passes between the previously described first drive system and second drive system of the card infeed system 240 (FIG. 8) (e.g., as the card passes between the second advancing roller 56 and the third advancing roller 72), as shown in FIGS. 4A and 4B. Of course, those of ordinary skill in the art will recognize that the sensor 210 may be placed at other suitable locations along the path the card travels within the card-handling device 10.

By way of example and not limitation, the card recognition system may include a two-dimensional image sensor comprising, for example, a camera device that includes a complementary metal oxide semiconductor (CMOS) image sensor or a charge-coupled device (CCD) image sensor. For example, the card recognition system may include a video camera imaging system as described (or substantially similar to that described) in U.S. patent application Ser. No. 10/623,223, filed Jul. 17, 2003 (which was published Apr. 8, 2004 as U.S. Patent Publication No. US2004/0067789A1), the disclosures of each of which are incorporated herein in their entirety by this reference. As described therein, one suitable card recognition system comprises the camera sold under the trademark "DRAGONFLY®" and available from Point Grey Research Inc. of Vancouver, British Columbia, Canada. The DRAGONFLY® camera includes a 6-pin IEEE-1394 interface, and an asynchronous trigger. This camera can be used to acquire images using multiple frame rates, to acquire 640×480 or 1024×724 24-bit true color images, or to acquire 8-bit gray scale images. Furthermore, the DRAGONFLY® camera is typically provided with image acquisition software and exhibits plug-and-play capability. Such a commercially available camera may be combined with commercially available symbol recognition software, which may be executed using an external computer (not shown). Such commercially available image recognition software may be "trained" to identify conventional playing card symbols and to classify and report each acquired image pattern as a specific card suit and rank. The graphics used to identify rank and suit of each card are not identical or standard and may vary between decks of cards. Once an image recognition software program for identifying rank and suit has been developed, the software program may be configured to allow the software program to be trained for each particular deck of cards to be handled by the card-handling device 10 to enable the software program to accurately identify rank and suit of the particular cards used. Such training of the software program may be done at the casino table or by a security team before the card-handling device 10 is placed on a table.

As yet another example, the sensor 210 may include a one-dimensional image sensor such as a line scanning system or device that includes a contact image sensor (CIS), as disclosed in U.S. patent application Ser. No. 11/152,475, filed Jun. 13, 2005, now U.S. Pat. No. 7,769,232, issued Aug. 3, 2010, and U.S. patent application Ser. No. 11/417,894, filed May 3, 2006, now U.S. Pat. No. 7,593,544, issued Sep. 22, 2009, the disclosures of each of which are incorporated herein in their entirety by this reference. Such line scanning systems may operate in conjunction with additional card position sensors. Sensors that may be used to identify a card position at the time a line scan is performed by the line scanning system are commercially available. Such line scanning systems may be small enough to be entirely incorporated into the card-handling device 10 without requiring used of an external computer for executing an image recognition software program.

Figure 10:
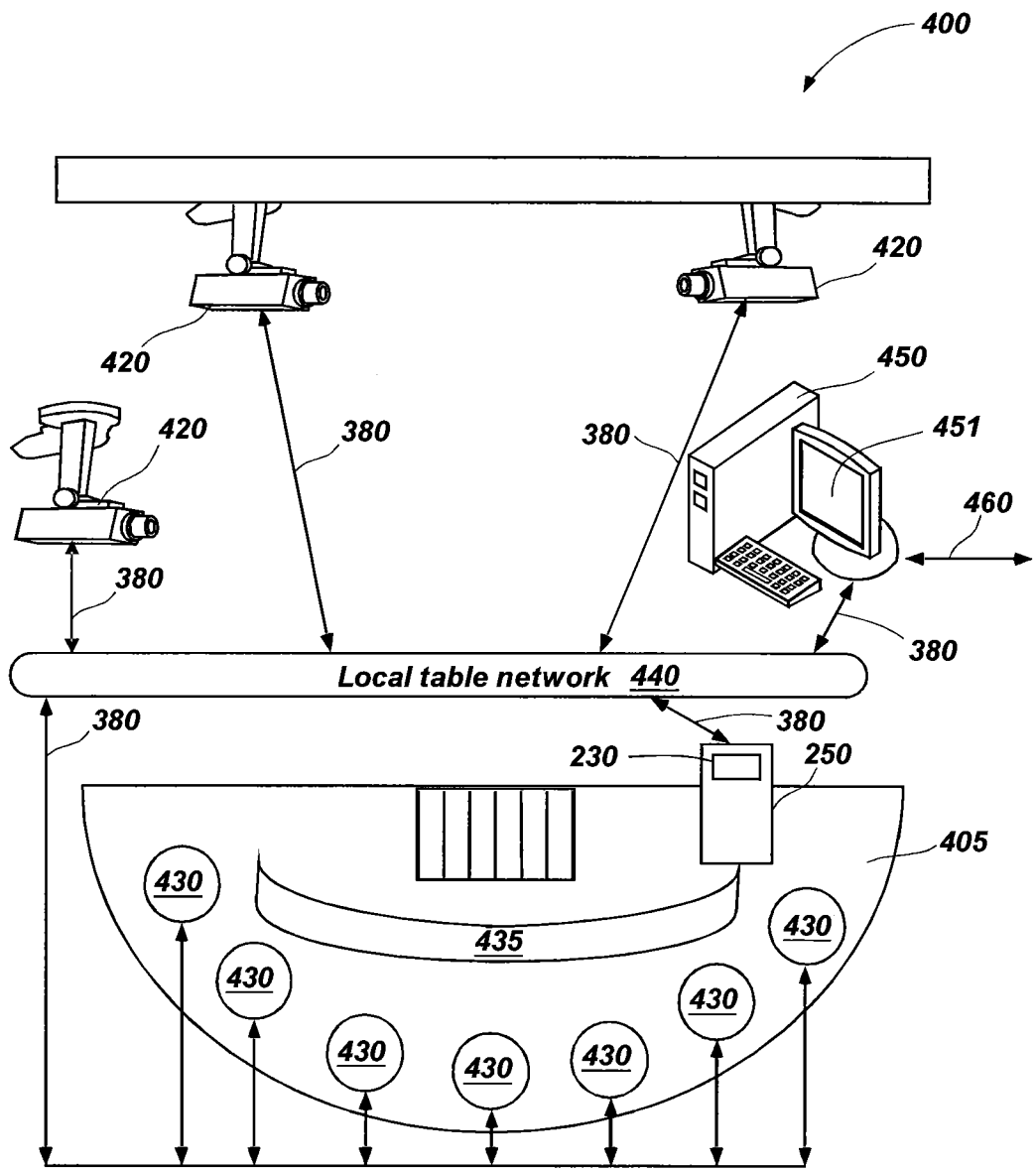
FIG. 10 illustrates a layout of a casino table game and possible placement of elements of an integrated monitoring system used to monitor gaming at a casino table in accordance with embodiments of the present invention.

The sensor signals may be processed by a separate hardware element (not shown) such as a Field Programmable Gate Array (FPGA) or an Application Specific Integrated Circuit (ASIC) using the methodology described in U.S. Patent Publication US 2005/0242500 A1, now U.S. Pat. No. 7,769,232, issued, Aug. 3, 2010, the content of which is incorporated by reference herein. Alternatively, the sensor signals may be processed by a processor 222 (FIG. 8) within the card-handling device 10 or by an external computer system, such as, for example, a table manager 450 (FIG. 10).

In some applications, the cards to be handled by the card-handling device 10 may be standard unmarked conventional cards, and the sensor 210 may be configured to sense and identify only a conventional rank and suit of each card. In additional applications, the cards to be handled by the card-handling device 10 may be marked with ultraviolet (UV), infrared (IR), near infrared (near-IR), or visible wavelength inks or may have embedded radio frequency identification (RFID) tags, magnetic coding, bar codes, embedded electronic devices, or any other marking means, and the sensor 210 may be configured to detect at least one such marking in addition to, or instead of, identifying a rank and suit of each card. The card recognition system also may be configured to sense, detect, and identify cards that have been physically damaged (e.g., due to wear) and/or cards that have been marked in any way that facilitates cheating. The card recognition system may be configured to sense and identify cards that include one or more of cuts, abrasions, bends, dirt, debris, and/or to verify that each card exhibits an expected, predefined color, thickness, reflectivity, mass, or other identifying characteristic or feature.

The card recognition system may be configured to communicate electrically with the subsequently described control system. In addition, multiple sensors 210 may be useful for redundancy, better overall image fidelity, or simply for advantageous placement of the type of sensor. For example, a 2-dimensional sensor may be more practical in a position where it may read the card in a stationary position. On the other hand, the CIS module may be more practical in a position where it reads the card while it is in motion to enable the line scans at various positions along the rank and suit designators on the card.

The card-handling device 10 may further include a control system 220. The control system may configured to receive input signals from a user, to receive input signals from one or more of the various sensors described herein, and/or for selectively controlling one or more of the various previously described active components of the card-handling device 10.

FIG. 8 is a schematic block diagram of one example of a control system 220 that may be used with the card-handling device 10 shown in FIG. 1 to create a card-handling and analysis system 250. In some embodiments, the entire control system 220 may be physically located within the card-handling device 10. In other embodiments, one or more components of the control system 220 may be physically located outside the card-handling device 10. Such components may include, for example, a computer device (e.g., a desktop computer, a laptop computer, a handheld computer (e.g., personal data assistant (PDA), network server, etc.). Such external components may be configured to perform functions such as, for example, image processing, bonus system management, network communication and the like.

As shown in FIG. 8, the control system 220 may include at least one processor 222 (e.g., a microprocessor or microcontroller). The control system 220 also may include memory 224 for storing information such as software and data to be read or written by the processor 222. The control system 220 also may include one or more input devices 226 and one or more output devices 228. By way of example and not limitation, the one or more input devices 226 may include a keypad, a keyboard, a touchpad, a button, a switch, a lever, and the like. An input device 226 may include an authorization element. An authorization element may be used to limit access to some of the functions, such as, for example, recalling the content of current or past hands. As a non-limiting example, authorization element input device 226 may be configured to read the information on a magnetic card strip and send that information to the control system 220. The information on a magnetic card strip may include a user identification. The control system 220 can verify that the card information belongs to a database of authorized users. Other non-limiting examples of authorization elements include a fingerprint scan, a Radio Frequency Identifier (RFID) scan, and a retina scan. A general security element for identifying an authorized user may include one or more authorization elements or it may include one or more authorization elements in combination with the entry of a password by the authorized user.

The authorization element input device 226 may be integrated as a part of the control system 220 or it may be configured as a stand-alone device in communication with the control system 220 across a wired or wireless communication medium.

The one or more output devices 228 may include a graphical display 230 (i.e., a screen or monitor), a printer, one or more light-emitting diodes (LEDs), a device for emitting an audible signal, etc. In some embodiments of the present invention, the input devices 226 and the output devices 228 may be integrated into a single unitary structure, such as, for example, with the display 230 configured as a touch screen display 230.

The touch screen display 230 may be located below the gaming table surface when the card-handling device 10 is mounted to a gaming table in the manner previously described herein. The display 230 may be used to output information to a dealer or other user regarding information such as the identity of the cards that have been dealt into each hand, which may allow the dealer to assess whether the cards shown or played by that player are different (indicating that the cards have been changed or swapped) without alerting the player. For example, if a deviation between a dealt hand and a displayed or played hand were to occur, indicating a confirmed case of card switching, the dealer would be able to notify security without the player's knowledge, which may allow the cheating player to be apprehended. By providing or locating the display 230 below the surface of the table and/or facing away from the players at the table, the display 230 may be concealed to the players, and important information may be conveyed to and from casino personnel without the knowledge of the players. Touch screen controls on the display 230 also may provide a larger number of input options for the user, as compared to more standard push button controls. The display 230 may be capable of displaying alphanumeric information, graphical information, animation, video feed, and the like.

As another input option, the touch screen may be used to present login information for an authorized user. Such information may include a user identification, a password, or a combination thereof. As a non-limiting example, the touch screen may prompt a user to enter a user identification and a password. As another non-limiting example, the presentation and acceptance of login information may be used in combination with the authorization element input device 226 such that the user identification is received from the magnetic card or other authorization element and the password is entered by the authorized user. In this combination, the database of authorized users may be checked to determine that the entered password corresponds with the user identification on the magnetic strip.

As another non-limiting example, the control system 220 may be configured with a factory default password. After entry of the factory default password, custom password information may be entered, such as, for example, to create authorized user passwords. In some embodiments, the default password may only allow access to operations for entering the custom passwords. In these embodiments, entry of a custom password may be required to access hand information.

As shown in FIG. 8, the control system 220 may be configured to communicate with each of the previously described card infeed system 240, card output system 242, temporary card storage system 244 or device, and card recognition system 246. In this configuration, the control system 220 may be configured to receive input signals from a dealer or other user, signals from the various sensors of the card-handling device 10, and to coordinate and control operation of the card infeed system 240, the card output system 242, the temporary card storage system 244, and the card recognition system 246 so as to perform various card-handling operations such as, for example, shuffling of cards placed in the card infeed tray, sorting cards placed in the card infeed tray, and/or forming and sequentially dispensing playing hands from cards placed in the card infeed tray.

The control system 220 may be configured to communicate across any wired or wireless communication medium 380 to a network 440. By way of example, and not limitation, communication media may include serial data links, parallel data links, Ethernet, a Wide Area Network (WAN), a Local Area Network (LAN), BLUETOOTH®, Wi-Fi, WiMax, and other suitable communications links. In some embodiments, communication on the communication medium may be implemented with a substantially stand-alone hardware element (not shown). In other embodiments, the communication may be accomplished with a combination of hardware and firmware/software.

The network 440 also may be used to collect and/or process data from other data collection devices on a gaming table such as, for example, radio frequency identification (RFID) wager amount sensors, object sensors, chip tray inventory sensors, and the like, as is explained more fully below in the description of FIG. 10. Data may be collected by the control system 220 and sent to a remote database for later analysis and processing, or the data may be analyzed in real time.

The processors 222 may be implemented as microcontrollers including memory for storage of data and firmware/software for execution thereon. The processors 222 also may be implemented as microprocessors with separate memory 224 for storage of the data and firmware/software. In addition, the processors 222 may incorporate an ASIC, Field-Programmable Gate Array (FPGA), multiple Programmable Logic Devices (PLD), and combinations thereof.

In some embodiments, the processors 222 may be configured as two separate processors configured to perform different functions. A first processor may be configured for operating and controlling the functions of the shuffler, including operation of electrical devices such as motors, controlling the images displayed on the display 230, processing signals received from all internal sensors such as optical object presence sensors, motion sensors and the like. Thus, during operation, the first processor 222 may determine the random order in which cards are loaded into the compartments of the card-handling device 10.

The first processor may also control the display 230 including touch screen controls and may be configured as a further user interface for programming the processors to display additional game names and to dispense cards according to user inputted data.

A second processor (not shown) may be used to interpret information received from the card recognition system 246 to determine rank, suit, other card information, or combinations thereof. The first processor and the second processor may communicate with each other and collaborate so that the identity of each card and the compartment in which it is placed are associated.

Of course, those of ordinary skill in the art will recognize that with multiple processors 222, the task load may be allocated differently depending on performance characteristics and features of each of the processors 222. For example, a microcontroller may include features well suited for controlling and interfacing with external devices and a microprocessor may be well suited for performing signal processing functions such as image recognition.

In operation of embodiments of the present invention, the dealer will "deal" the hands from the card output tray to each player, such as in a preset order or by player position. Thus, embodiments of the present invention can track the cards from the shuffler to the player to determine the contents of each player's hand. In other words, through data manipulation, information relating to the content of each hand the shuffler dispenses is formed and is retrievable. The information collected from the card-handling device may be time stamped and stored accordingly. Moreover, this information may be stored internally on the card-handling device or on an external computer to provide a recall feature for any hand during a number of completed rounds of play. In some embodiments, a large database outside the shuffler may be maintained so that more history of hands dealt can be stored and later retrieved or analyzed.

As shown in FIG. 8, and as was described earlier, in some embodiments of the present invention, the card recognition system 246 may include a separate controller 212 (e.g., a separate signal processor, such as, for example, an FPGA for receiving signals from the sensor 210 (e.g., camera device or line scanning device)) to determine rank and/or suit of each card being read or sensed by the card recognition system 246. In additional embodiments, such functions may be performed by the processor 222 of the control system 220, or the controller 212 may be a separate controller that is integrated with the control system 220 and located remote from the sensor 210

The control system 220 of the card-handling device 10 may be configured under control of a computer program to enable a dealer or other user of the card-handling device 10 to perform any one of a number of functions or operations on a deck of cards using the card-handling device 10. The display 230 (or other input device) of the card-handling device 10 may include a menu that allows the dealer or other user to select what functions or operations the card-handling device 10 is to perform on a deck of cards placed in the card infeed tray 12. The functions or operations may include one or more of shuffling operations, sorting operations, and dealing operations, and recall of card information from various hands, rounds, or combinations thereof, as will be explained more fully below.

By way of example and not limitation, one function or operation that may be performed by the card-handling device 10 is a shuffling operation that includes a deck shuffle with the entire shuffled deck output to the card output tray 14. In other words, the control system 220 of the card-handling device 10 may be configured under control of a program to cause the card-handling device 10 to randomly shuffle an entire deck of cards placed in the card infeed tray 12, and to dispense the entire deck of shuffled cards into the card output tray 14.

By way of example and not limitation, the card-handling device 10 may be used to shuffle cards placed in the card infeed tray 12, the control system 220 of the card-handling device 10 may be configured to read or sense one or more identifying characteristics or features of each card as the card is carried past the card recognition system 246, as previously described herein, and to randomly rotate the carousel 120 while inserting the cards to insert cards sequentially into the next compartment 127 of the carousel 120. After all the cards have been randomly placed into compartments 127 of the carousel 120, the control system 220 may cause the carousel 120 to spin or rotate in a step-wise motion as the card output system 242 ejects cards out from the compartments 127 of the carousel 120 either randomly or sequentially. In other words, the cards may be placed in a randomized or shuffled sequence as they are placed into the carousel 120. In this manner, the cards or groups of cards may be provided in the card output tray 14 in a random, shuffled sequence.

Yet another function or operation that may be performed by the card-handling device 10 is a dealing operation that includes a sequential output of randomly generated playing hands (or other subsets of cards) to the card output tray 14, each hand or subset of cards comprising a predetermined number of cards. In other words, the control system 220 of the card-handling device 10 may be configured under control of a program to cause the card-handling device 10 to dispense a first randomly generated playing hand or subset into the card output tray 14. A second randomly generated playing hand may be output to the card output tray 14 after the control system 220 receives a signal from the sensor 200 indicating that the first randomly generated playing hand has been removed from the card output tray 14. This process may continue until a selected number of randomly generated playing hands has been dispensed and removed from the card output tray 14. If the game being played requires other sets of playing cards, such as, for example, a set of flop cards, dealer cards, common cards, extra player cards, etc., such sets of cards also may be generated and dispensed into the card output tray 14 in the sequential manner described above to prevent the sets of cards from being mixed with other playing hands or sets of cards. After the last playing hand or set is delivered, any cards from the deck or decks that remain in compartments 127 of the carousel 120 may be automatically unloaded to the card output tray 14, or the remaining cards may be unloaded to the card output tray 14 upon receiving an input signal from the dealer or other user (for example, an input signal generated by touching a predefined button on the touchpad display 230).

In some embodiments of the present invention, the control system 220 (FIG. 8) of the card-handling device 10 may be programmed to handle a particular deck of cards, such as, for example, a conventional deck of 52 playing cards comprising suits of spades, clubs, diamonds, and hearts, each suit comprising cards ranking 2, 3, 4 . . . 10, jack, queen, king, and ace. By way of example and not limitation, when such a deck of cards is placed into and detected within the card infeed tray 12 of the card-handling device 10, the control system 220 (FIG. 8) may be configured under control of a program to electronically generate a random or shuffled sequence of the deck, and to identify the playing hands (or other subsets of playing cards) that would be generated and dealt if the electronically shuffled deck of cards were actually physically dealt to the players (and the dealer himself) by the dealer. The control system 220 then may assign one compartment 127 of the carousel 120 to each of those hands or subsets of playing cards (which may be referred to as "hand compartments." Then, as the cards are fed into the card-handling device 10 and identified by the card recognition system 246, the control system 220 may cause the carousel 120 to selectively rotate such that any cards corresponding to the hands or subsets are placed within the corresponding hand compartments 127 of the carousel 120. Other cards not corresponding to hands or subsets of cards may be placed in one or more of the other compartments 127 of the carousel 120 not designated as hand compartments. The control system 220 then may cause the card output system to dispense the first hand or subset of cards within the first hand compartment 127 into the card output tray 14. After the dealer has removed the first hand from the card output tray 14 and given that hand to the corresponding first player, the control system 220 then may cause the card output system to dispense the second hand or subset of cards within the second hand compartment 127 into the card output tray 14. This process may continue until a selected number of randomly generated playing hands has been dispensed and removed from the card output tray 14 and dealt to the table.

The display 230 may include a touch screen or other user controls that may be used to program the control system 220 of the card-handling device 10. For example, the card-handling device 10 may be programmed to sequentially deliver a specified number of hands each comprising a specified number of players. Furthermore, the card-handling device 10 may be programmed to deliver a specified number of cards to a dealer, a specified number of flop cards, a bonus hand, common cards, or any other card or cards used in the play of a casino card game. The touch screen or other user controls of the display 230 also may be used to input a name of a game for which the card-handling device has been programmed, so that the name of the programmed game appears on the display 230 in a menu of user selectable games. By employing a control system 220 that is programmable by an end user as described herein, the need for factory programming or re-programming of the card-handling device 10 every time a new casino card game is developed may be eliminated, which may save time, eliminate the need for re-submission of software to various gaming agencies for approval before implementation in a casino, and eliminate the need for upgrading software in the field.

By way of example and not limitation, the card-handling device 10 may be programmed by an end user to deliver cards in a pattern or sequence corresponding to the game of THREE CARD POKER®, which requires that the players and dealer each receive three cards. If a new game that utilizes three player cards (each) and three dealer cards were to be developed in the future, an end user would be able to input information including the new game name into the card-handling device 10 and the card-handling device 10 would be configured for playing such a game without requiring a software change.

Figure 9:
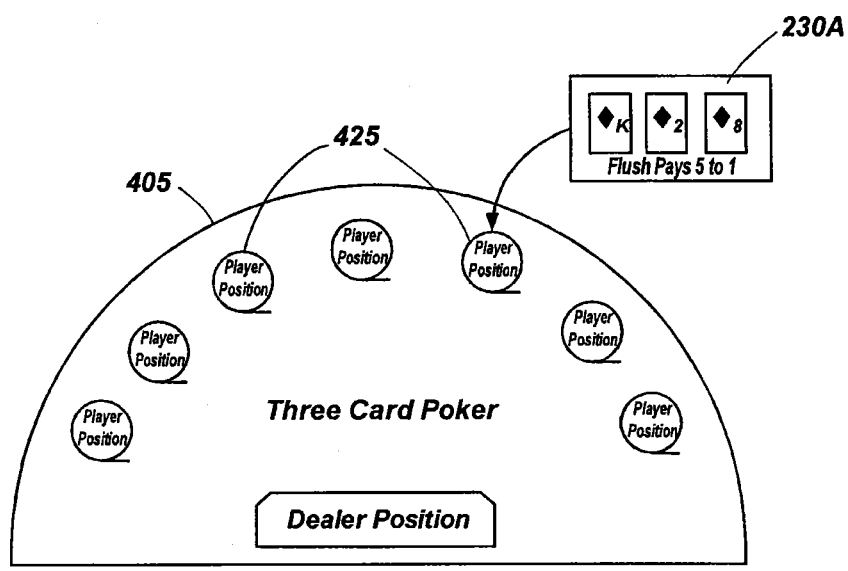
FIG. 9 illustrates a casino table game layout and possible placement of player positions.

As shown in FIG. 9, and also with reference to FIG. 8, the display 230 may be configured to display an image of a game table 405 with various player positions 425, such as the THREE CARD POKER®.

In one embodiment with a touch screen display 230, the card-handling and analysis system 250 may be configured such that the user may touch a region near a specific player position 425 and the display 230 may display card information 230A for the hand at that specific player position 425. Alternatively, each of the player positions 425 may display the card information of the hand at each player position 425.

As a non-limiting example, the content of the graphic may include the name of the game, player positions, dealer position, and even game rules. A user may touch a specific player position that is displayed on the touch screen to reveal the hand to which this position was dealt. The display may also show the result of the game, and the associated payouts, for example, a flush on a "Three Card Poker" table may pay 5 to 1.

As another non-limiting example, the touch screen display content may include navigation buttons such as "past rounds," "current round," played hands," "unused hands," "back," "forward," and "exit." The Played hands button may be used to display the hands that were actually dealt and bet upon in the current or a previous round. Similarly, the unused hands button may be used to display hands that may have been processed by the shuffler but never used in a round of play.

As non-limiting examples, the back button and forward button may be used to navigate among unused hands or played hands. Similarly, the back button and forward button may be used to navigate among previously played rounds that are stored in a database of rounds.

FIG. 10 is a block diagram of an integrated monitoring system 400 (also referred to as a table management system) used to monitor a gaming table 405 (shown in FIG. 7). The integrated monitoring system 400 includes a card-handling and analysis system 250 coupled to a table manager 450 through a local table network 440. Some embodiments of the integrated monitoring system 400 may also include one or more table image units 420 and object recognition device 430 (e.g., chip readers) coupled to the table manager 450 through the local table network 440. The table manager 450 may be coupled to a server (not shown) through a communication network 460. By way of example, and not limitation, the communication network 460 may be configured to couple multiple table managers 450 to a central database or server by creating a network for a specific pit area, a specific casino floor area, or the entire casino.

The overhead imaging equipment and other hardware and/or software is used to extract game information from a live gaming table. Data from the overhead imaging equipment may be processed to extract game play information. Non-limiting examples of game play information include but are not limited to: player position occupied, wager placed at a given player position, movement of a card or group of cards from a shuffler (or card-reading shoe) to a player position, movement of a card or cards to a common card area, movement of a card or cards to a dealer card area, movement of a card or cards to a bonus card area, placement of a side wager, withdrawal of a wager, rolling of a dice, spinning of a wheel, moving of cards from one area to another area on the table, the collection of cards at the conclusion of a round of play, dealer hand signals, the payment of payouts and the taking of lost wagers, etc.

U.S. patent application Ser. No. 11/558,810, filed Nov. 10, 2006, and titled "Casino Table Game Monitoring System," describes comprehensive card game monitoring systems, including suitable hardware and software for performing the overhead imaging function. Data such as the card composition (for games dealt—face up) and wager information from such a system is collected and used in combination with the hand composition information derived from the card-reading system of shufflers of the present invention to form data records of historical hand composition for a given player position. The content of this application is incorporated by reference in its entirety.

Card composition data from the overhead imaging system may be compared to the card composition information collected in the shuffler to determine if illegal card swapping has occurred. The data from the overhead imaging system can also be used to associate the hand with a particular player position on the table. Additionally, data from the overhead system may be used to verify a hand composition prior to making a large payout.

The combined data may be stored in memory associated with a processor within the card shuffler or transmitted via a hardware, wireless or network connection to an external database. In one example of the invention, a finite number of hands (i.e., 8-10) per player position is stored in the internal memory of the shuffler and can be displayed on the display associated with the shuffler. Any information that is not stored in the shuffler memory may be instead stored in the external database of an external computer and may be displayed on a display associated with the external computer. In some embodiments, the information stored in the external database may be recalled and displayed using the user inputs of the shuffler, allowing the previously stored information to be displayed on the shuffler display.

A layout of a blackjack table 405 is shown as a non-limiting example of another possible casino table game to which embodiments of the present invention may be applied. The layout illustrates one contemplated, suitable arrangement of elements of the integrated monitoring system 400 in accordance with an embodiment of the invention. The integrated monitoring system 400 may include many components for determining various forms of information about the game being played at the table 405, the players playing the game, wager amounts and payouts, and the dealer responsible for the game. As is described below in more detail, the information may be captured, processed, and acted upon (e.g., generation of alerts) in substantially real time.

In system 400, the table 405 is used for blackjack and is equipped with the card-handling and analysis system 250 (FIG. 8) described earlier. The card-handling and analysis system 250 with display 230 is configured for communications via communication medium 380 and the local table network 440 with the table manager 450. The system 400 may include an object recognition device 430. As one example of an object recognition device 430, FIG. 10 illustrates object recognition devices 430 that may be configured as Radio Frequency Identifier (RFID) antennas/transmitters for each wagering area. In an embodiment with RFID transmitters 430 and RFID tagged chips (not shown), the RFID transmitters 430 are located within or underneath the table 405. The RFID antennas/transmitters respectively read the values of the game chips and then transmit the chip information to the table manager 450 via the communication medium 380 and local table network 440. U.S. Pat. Nos. 5,651,548 and 5,735,742 describe RFID chips and chip reading systems that may be used as the game chips and RFID transmitters 430. Although not shown, the RFID transmitters 430 may be configured to extend into an insurance area 435 of the table 405 to obtain the chip values of insurance wagers. In another embodiment, additional individual RFID transmitters connected to the communication medium 380 may be placed in the insurance area 435, one RFID transmitter associated with each player wagering area.

The system 400 may also include overhead cameras 420 (also referred to as image units) connected to a ceiling of the casino, mounted on a pole to the table, or in the vicinity of the table 405. These cameras 420 process the images received by the cameras 420 respectively and communicate with the table manager 450 over the communication media and the local table network 440.

The table manager 450 processes, and may transmit, images of items viewed by the cameras 420 in substantially near real time. Dealt card values, wagers, and other table activity can be imaged and determined using the cameras 420 in cooperation with the table manager 450. The table manager 450 may be implemented as a general-purpose computer system, a server, or other processor system as is generally known in the art. The table manager 450 will contain computer implemented processing that may be stored on a computer-readable medium of the general-purpose computer system. As such, the processing and functions of the table manager 450 may be stored as a computer program on a computer-readable medium, or downloaded from the server (not shown) over the communication network 460.

As can been seen from FIG. 10, the cameras 420 are positioned to achieve a full view of the gaming table surface, and may be positioned to give the best vantage point for the desired application. An optical or magnetic synchronizing sensor can be used to detect the presence of an object on the gaming surface of the table 405. The sensor, if used, may activate the cameras 420 and trigger image acquisition. The images are processed and transmitted to the table manager 450.

As with the control system 220 (FIG. 8) of the card-handling device 10 (FIG. 1), the integrated monitoring system 400 may be configured with an authorization element input device (not shown). As a non-limiting example, the authorization element may be in communication with the table manager 450. Thus, in the integrated monitoring system 400, the table manager 450 may be configured for handling the authorization process of gathering a user identification, a password, or a combination thereof. The result of the authorization process may then be sent to the card-handling and analysis system 250.

Figure 11:
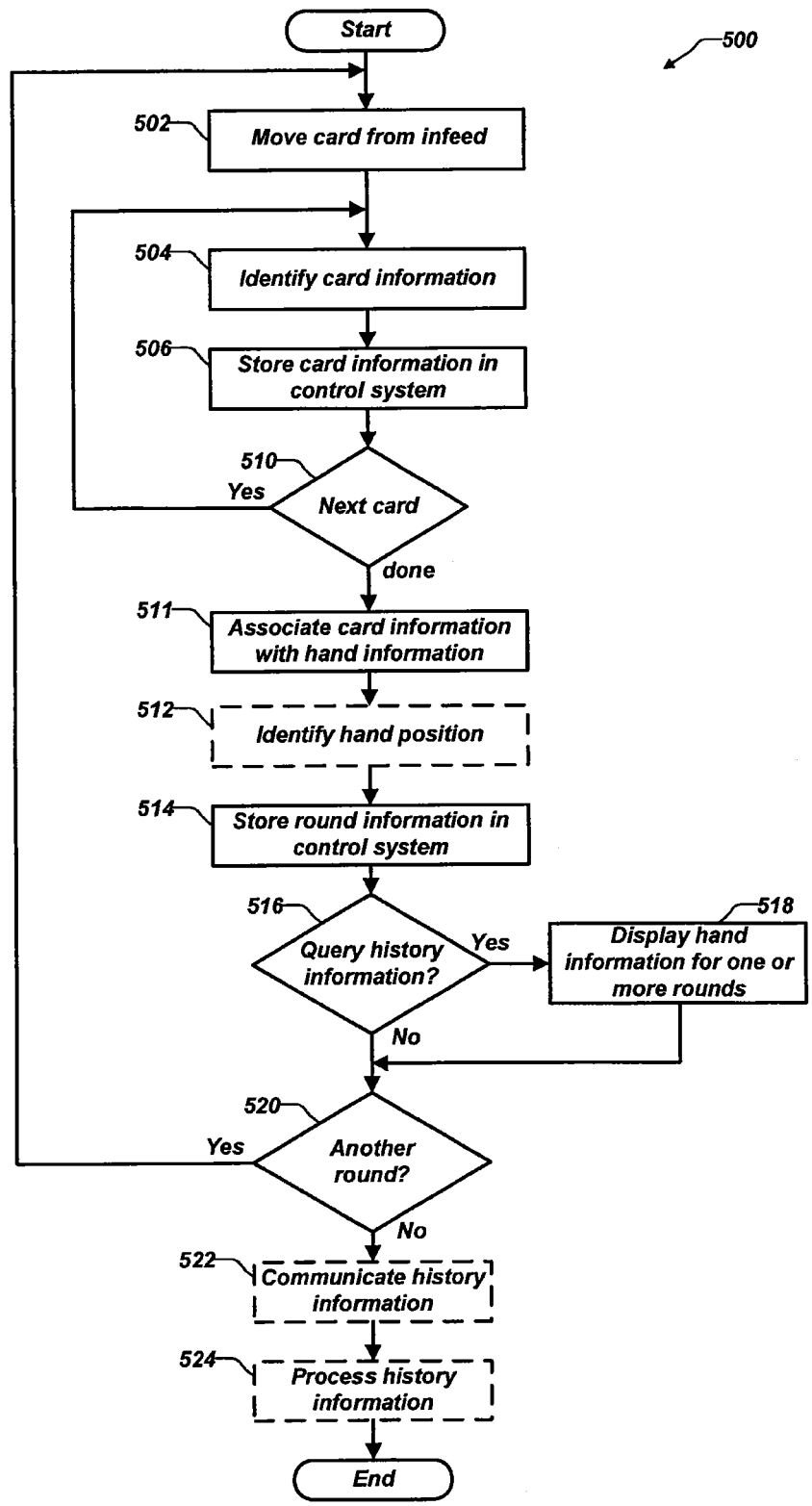
FIG. 11 is a flow diagram of a method of recognizing card information and maintaining a play history in accordance with embodiments of the present invention.

FIG. 11 is a flow diagram of a method of recognizing card information and maintaining a play history in accordance with embodiments of the present invention. Many of the operations illustrated in FIG. 11 may be performed anywhere within the process and are shown in the sequential order of FIG. 11 only for ease of description. At operation 502 the cards are moved from the infeed of the card-handling device and through at least part of the card-handling device. At operation 504, the card recognition system identifies information for each card as it moves through the card-handling device or at some specific location within the card-handling device. Any suitable location within the card-handling device may be used as long as the card information collected may be associated with a specific card and a specific hand or group of cards.

Operation 506 indicates that the card information from the card recognition system may be analyzed to determine card features, such as, for example, rank and suit, and the card information is stored in the control system.

Decision 510 determines whether another card should be processed for the current round. If so, control returns to operation 504 to process the next card. If after loading and the proper number of cards are present for the current round, control continues on to operation 511. The loop controlled by decision 510 may be used, as a non-limiting example, to process each card in a standard 52 card deck to verify that the deck is complete. This may be done by comparing the rank and suit of each card with a library of stored information. If a card is missing from the deck, the rank and suit of that card may be displayed and the shuffle may be aborted.

In other words, as each card is processed by the device, a processor (or process) associated with controlling the card-handling device can track where each card that is handled ends up in the carousel 120 (FIG. 4A). In addition, another processor (or another process) can keep track of the card information for each card. As a result, the loop controlled by decision 510 can verify a full deck is present based on the card information (e.g., rank and suit).

At this point, some embodiments may maintain the process of identifying which card went where in the carousel separate from the process of identifying the card information for each card. As a non-limiting example, suppose the cards are numbered sequentially with a card number as they are delivered to the carousel. The first process may track the random distribution of cards. For example, the first process could track that card 1 is delivered to compartment 8, card 2 is delivered to compartment 3, card 3 is delivered to compartment 1, and so on. The second process may track that card 1 is a two of diamonds, card 2 is a king of clubs, card 3 is a five of hearts and so on. With this tracking, as a security feature, the overall process 500 may not know complete information about what each hand contains. Rather, one process may know that a hand contains cards 3, 8, and 51. The other process may know the specific rank and suit of each card in the sequence of card numbers.

After completion of verification of the deck and recording of card information for each sequential card, control passes to operation 511.

In operation 511 the card information for each sequential card may be associated with the hand information of which card numbers are in which compartments of the carousel. In other words, as a non-limiting example, the information that compartment four contains cards 3, 8 and 51 is combined with the information that card 3 is a queen of hearts, card 8 is a ten of clubs, and card 51 is a nine of spades.

Some embodiments may perform this operation of associating the hand information with the card information as late as possible in the round to prevent cheating where the information may be known before the hands are actually dealt to the players. Thus, the association may be made at different point in execution of playing the round, such as, for example, after the hands are complete in the carousel, as a hand as it is removed from the card-handling device, as a hand is placed in a player position, or after all hands have been dealt.

In other embodiments of the invention, instead of associating the card information of all cards with all the card numbers, the association process may only be performed for the card information associated with cards that are dealt into compartments forming hands. The rank/suit information of the unused cards (i.e., the cards that go into discard compartments) may not be matched up.

In still other embodiments, the card information may be associated directly with the compartment number rather than keeping track of the card information and hand information separate. Either way, after all cards have been distributed, the hand compositions are known by the processor. As a matter of design choice, this information is not viewable to the end user until after the cards have been distributed into the delivery tray.

Optional operation 512 indicates that the hand positions may be identified for the hands before, after, or when they are dealt from the card-handling device. If the embodiment is configured with an object recognition device, the hand position may be determined based on active player positions as is described above with reference to FIG. 10.

Operation 514 indicates that all card information and player position information may be stored for the entire round after the round is complete. As a non-limiting example, such information may include, the type of game, player position, card rank and suit of each card in each player position's hand, size of bet at each player position, and anticipated payout based on the rules.

Decision 516 indicates whether a query is made for history information. This history information may include card information and player position information for the current round or for past, completed rounds. If display of history information is desired, operation 518 displays the desired information. Otherwise, control transfers to decision 520. The display information may include a display of all hands for the current round or only hands at active player positions. Furthermore, the display may be configured to display a single player's current hand or past hands.

In some embodiments, the display may display the card information by presenting some type of graphical representation or symbol for the card information such as rank and suit. In other embodiments, all or part of a stored image of the card may be displayed rather than just the rank and suit symbols. For example, a graphic image of a one-eyed Jack of diamonds can be displayed rather than a "J" and a diamond symbol. In a preferred embodiment, only a portion of the graphic image is displayed (e.g., 25% of the card face).

In addition, the shuffler or an external game controller in communication with the shuffler processor may be programmed with the game rules such that the shuffler can display the game result information or send data to an external display. In a preferred format, the game rules are programmed into the shuffler processor such that the winning hand can be identified on the shuffler display. Even if an external processor determines a game result, the data can be transmitted back to the shuffler so that the game outcome can be displayed on the shuffler display and so that the display can indicate to the dealer who should be paid and the correct payment amount.

Decision 520 indicates whether another round is desired; if so, control transfers back to operation 502, otherwise, control transfers to operation 522. Optional operation 522 indicates that the history information gathered and stored in the control system 220 (FIG. 8) or table manager (FIG. 10) may be transferred to another computer for archiving or additional processing. As a non-limiting example, the control system 220 may include a history of about 10 rounds. If the control system 220 is in communication with an external computer, the control system 220 may send the round information for rounds older than the past 10 rounds to the external computer. Otherwise, the control system 220 may simply drop off the oldest round beyond the 10th round.

Optional operation 524 indicates that additional processing on the history may be performed. Additional processing may include, as non-limiting examples, review of the history in an attempt to find dealer errors, cheating, and statistical review of the history to find betting patterns or to verify randomness of the game. Furthermore, this additional processing may be performed on an external computer, the table manager 450 (FIG. 10) or the control system 220 (FIG. 8). In one embodiment, historical hand composition information is stored within control system 220, and is accessible by the user by inputting a request on user input device 226. A touch screen display 230 displays historical hand information upon request. In one embodiment, multiple historical hand compositions for each player position are viewable.

In another embodiment, historical hand composition information is stored on table manager 450 (e.g., controller) and is displayed on either a separate monitor 451 or on the shuffler display 230.

In some embodiments, a shuffler may be configured to deliver no more hands or other card combinations (such as dealer hands, community cards, bonus hands, bonus cards, etc.) than is necessary to administer the game. For games that do not require the dealer to deal hands to all table positions (regardless of whether there is an active player), the shuffler may receive a signal from the wager sensors (or other sensor denoting an active player position) and limits the hand output to only what is necessary to administer the game. As a non-limiting example, if there are only two players, the shuffler will sense that state and deliver only two hands.

Although the embodiments of the invention may have been described with reference to particular card games, it should be appreciated that they may be applicable to any other casino communal or non-communal card games.

While the embodiments of the invention have been described in detail in connection with preferred embodiments known at the time, the invention is not limited to the disclosed embodiments. Rather, the invention can be modified to incorporate any number of variations, alterations, substitutions, or equivalent arrangements not heretofore described, but which are commensurate with the scope of the invention. Accordingly, the invention is not limited by the foregoing description or drawings, but is only limited by the scope of the appended claims, including equivalents thereof.

What is claimed is:

1. A secure card game monitoring apparatus, comprising:
a card infeed tray;
a card output tray;
a card-handling system configured to deliver randomized sets of cards as a group to the card output tray;
a control system configured to control operation of the apparatus;
memory associated with the control system;
a card recognition system in communication with the control system and the memory, the card-recognition system configured to automatically read card information and store the card information in the memory, the card information including rank and suit information;
an input device in communication with the control system; and
an authorization element configured to limit user access to data stored in the memory of the control system.

2. The apparatus of claim 1, wherein the authorization element comprises a card reader system.

3. The apparatus of claim 1, wherein the authorization element is selected from the group consisting of a retina scanner, an RFID scanner, a card reader, and a fingerprint scanner.

4. The apparatus of claim 1, wherein the card-handling system comprises a plurality of compartments, each compartment configured to receive cards.

5. The apparatus of claim 1, wherein the control system is configured to store historical card set and round of play information in the memory for up to a predetermined number of completed rounds.

6. The apparatus of claim 5, wherein the historical card set and round of play information includes at least one of type of game, player position, card rank and suit of each card in each player's hand, betting information for each player, anticipated payout for each player based on game rules.

7. The apparatus of claim 1, wherein the authorization element is configured to limit user access to player hand data stored in the memory.

8. The apparatus of claim 1, wherein the authorization element is configured to limit user access to winning player hand data stored in the memory.

9. The apparatus of claim 1, wherein the control system includes at least one processor programmed to control the card-recognition system and the memory to keep track of the card information for each card and to keep track of hand information for where each card is located during handling by the card-handling system.

10. The apparatus of claim 9, wherein the at least one processor includes:
a first processor programmed to control the card-reading system and the memory to keep track of the card information for each card; and
a second processor programmed to control the card-reading system and the memory to keep track of the hand information for where each card is located during handling by the card-handling system.

11. The apparatus of claim 9, wherein the control system is configured to associate the card information and the hand information.

12. The apparatus of claim 1, wherein the control system is further configured to limit user access to data stored in the memory by requiring a user to input a password that is used in association with the authorization element.

13. A method of providing cards during a casino table game play, the method comprising:
controlling a card-handling device to handle a deck of cards and deliver randomized sets of cards as a group to an card output tray;
identifying hand information for the randomized sets of cards; and
controlling a card-recognition system to identify card information as cards from the deck of cards move through the card-handling device, the card information including rank and suit information.

14. The method of claim 13, further comprising receiving a user input through an input device.

15. The method of claim 14, further comprising limiting user access to data stored in the memory with an authorization element.

16. The method of claim 13, further comprising associating the card information and the hand information.

17. The method of claim 16, wherein associating the card information and the hand information occurs during a time that is selected from the group consisting of:
after the randomized sets of cards are completely formed within the card-handling device;
as the randomized sets of cards are removed from the card-handling device;
after an individual randomized set of cards is dealt to a player; and
after all randomized cards are dealt to all players of a round.

18. The method of claim 16, wherein associating the card information and the hand information is performed only for randomized sets of cards that are used in a round and not for unused cards in the round.

19. The method of claim 16, wherein storing the card information and storing the hand information are performed by separate processes.

20. The method of claim 13, further comprising storing historical card set and round of play information in the memory for up to a predetermined number of completed rounds.

21. The method of claim 20, further comprising sending historical card set and round of play information to an external computer for completed rounds that are older than the predetermined number of completed rounds.

22. The method of claim 13, wherein controlling a card-handling device to handle a deck of cards and deliver randomized sets of cards as a group to an card output tray includes randomly inserting the cards as groups into internal compartments of the card-handling device.

23. The method of claim 13, further comprising automatically displaying a winning hand and corresponding payout for a round of the casino table game.

24. A card game monitoring apparatus, comprising:
a card-handling device configured to:
randomize and dispense cards during a casino table game play; and
form a plurality of groups of cards, each group comprising a hand for a player position;
a card recognition system configured to recognize card information including a rank and a suit of each card while each card is under control of the card-handling device;
a control system comprising at least one processor and a memory, wherein the control system is configured to:
control the card-handling device; and
receive the card information for each card from the card recognition system; and
a display in communication with the control system and configured to display the card information corresponding to the hand information of at least one hand.

25. The card game monitoring apparatus of claim 24, wherein the card-handling device is further configured to form a hand in an internal compartment prior to being ejected from the card-handling device.

26. The card game monitoring apparatus of claim 25, wherein the card recognition system includes a device configured to sense card rank and suit information from each card as the card passes from an infeed tray to the internal compartment of the card-handling device.

27. The card game monitoring apparatus of claim 25, wherein the control system is further configured to electronically generate the card information comprising a hand prior to the card-handling device forming the hand in the internal compartment.

28. The card game monitoring apparatus of claim 24, wherein the display is further configured to automatically display game result information including a winning hand and corresponding payout.

29. A card game monitoring system, comprising:
   a card-handling device configured to randomize and dispense a plurality of groups of cards during a casino table game play, the card-handling device comprising:
      a card recognition system configured to recognize card information including a rank and a suit of each card while each card is under control of the card-handling device; and
      at least one processor programmed to receive the card information for each card from the card recognition system and determine card hand information comprising the cards in each group of cards used as hands in a current round;
   an object recognition device configured to identify at least one betting object indicating at least one active player position for the current round; and
   a table manager comprising a computer and configured to:
      receive position information about at least one active player position from the object recognition device;
      receive the card information from the card-handling device; and
      analyze the card information and the position information to display the card hand information for the at least one active player position; and
   a display configured to display the card hand information.

30. A method of providing cards during a casino table game play, the method comprising:
   causing a card-handling device to substantially automatically generate a plurality of groups of cards for a plurality of hands corresponding to a plurality of player positions;
   identifying card information including a rank and a suit of each card as each card moves through the card-handling device;
   identifying hand information for the cards in each group of a round of a casino table game;
   associating the hand information with the card information of the round; and
   displaying the card information corresponding to the hand information of at least one hand from the round.

31. A non-transitory computer-readable medium including computer-executable instructions that, when executed on one or more computers, perform the acts comprising:
   causing a card-handling device to substantially automatically generate a plurality of at least partial hands for at least one active player for a current round;
   identifying card information including a rank and a suit of each card as each card moves through the card-handling device;
   identifying a betting object indicating at least one active player for a current round; and
   displaying the card information of at least one at least partial hand from the current round.

32. A system for delivering cards to a casino game, comprising:
   a gaming table with a plurality of player areas, each player area of the plurality equipped with a sensor to detect an active player position;
   a shuffler configured to form and deliver hands of cards as a group of cards; and
   a processor programmed to direct the shuffler to deliver only a number of hands corresponding to a number of active player positions, as well as a dealer hand or common card positions when required by a rule of the casino game.

* * * * *